United States Patent [19]
Measamer et al.

[11] Patent Number: 6,117,158
[45] Date of Patent: Sep. 12, 2000

[54] RATCHET RELEASE MECHANISM FOR HAND HELD INSTRUMENTS

[75] Inventors: John P. Measamer; Robert L. Koch, Jr., both of Cincinnati; Robert F. Welch, Maineville; Anthony T. Nguyen, Cincinnati, all of Ohio

[73] Assignee: Ethicon Endo-Surgery, Inc., Cincinnati, Ohio

[21] Appl. No.: 09/349,028

[22] Filed: Jul. 7, 1999

[51] Int. Cl.$^7$ ................................................. A61B 17/28
[52] U.S. Cl. ............................................................ 606/208
[58] Field of Search .................................. 606/208, 205, 606/206, 207, 170, 167, 151; 81/331, 320, 323, 329

[56] References Cited

U.S. PATENT DOCUMENTS

| | | | |
|---|---|---|---|
| 804,229 | 11/1905 | Hutchinson . | |
| 1,659,112 | 2/1928 | Littlejohn | 30/12 |
| 5,176,702 | 1/1993 | Bales et al. | 606/208 |
| 5,314,424 | 5/1994 | Nicholas | 606/41 |
| 5,425,743 | 6/1995 | Nicholas | 606/208 |
| 5,476,479 | 12/1995 | Green et al. | 606/205 |
| 5,483,952 | 1/1996 | Aranyi | 606/131 |
| 5,735,874 | 4/1998 | Measamer et al. | 606/208 |
| 5,893,874 | 4/1999 | Bourque et al. | 606/205 |

*Primary Examiner*—Michael Buiz
*Assistant Examiner*—Kevin Truong

[57] ABSTRACT

A hand held surgical instrument for grasping and clamping tissue is disclosed. The surgical instrument has a handle body assembly and an elongated shaft. The shaft is connected to the handle body assembly at a proximal end and has an end effector at a distal end. The end effector is operably coupled to an actuation member extending from the handle body. The actuation member is moveable toward and away from the handle body to open and close the end effector. A locking tab is located on the handle body assembly and is moveable between a locked position and an unlocked position. A locking rod is movably engaged with a hole in the locking tab. When the locking tab is in the unlocked position, the actuation member is free to move towards and away from the handle body assembly to open and close the end effector. When the locking tab is in the locked position, movement to open the actuation member is prevented. The handle body assembly also has release trigger extending from the handle body assembly and operably coupled to the locking tab. The release trigger is moveable from a first position spaced away from the handle body to a second position adjacent to the handle body. The release trigger is normally biased toward the first position and is reciprocable, when initially squeezed toward the handle body assembly from the first position, to the second position, and subsequently released from the second position back to the first position. Consecutive reciprocations of the release trigger alternates the locking tab between the locked position and the unlocked position.

12 Claims, 19 Drawing Sheets

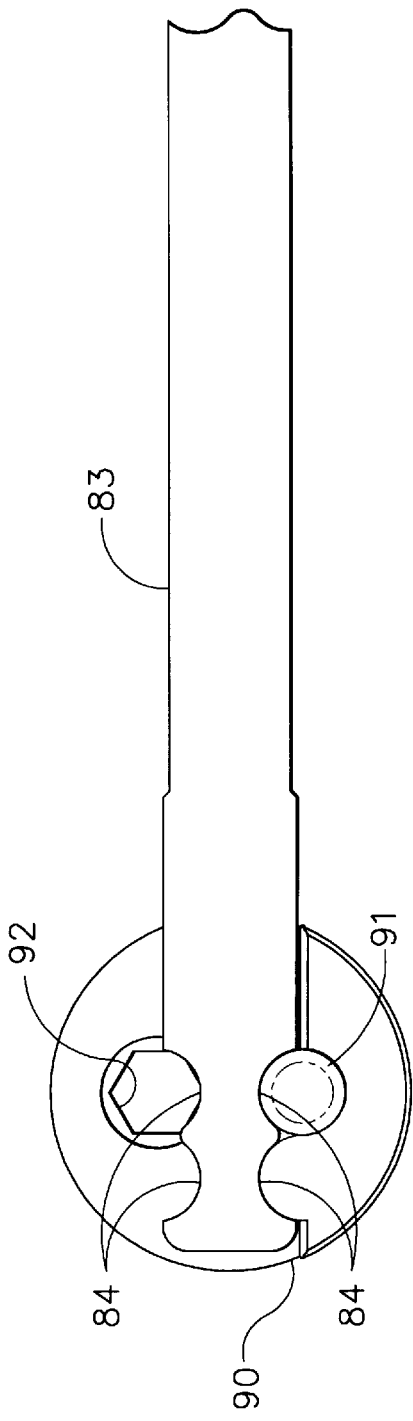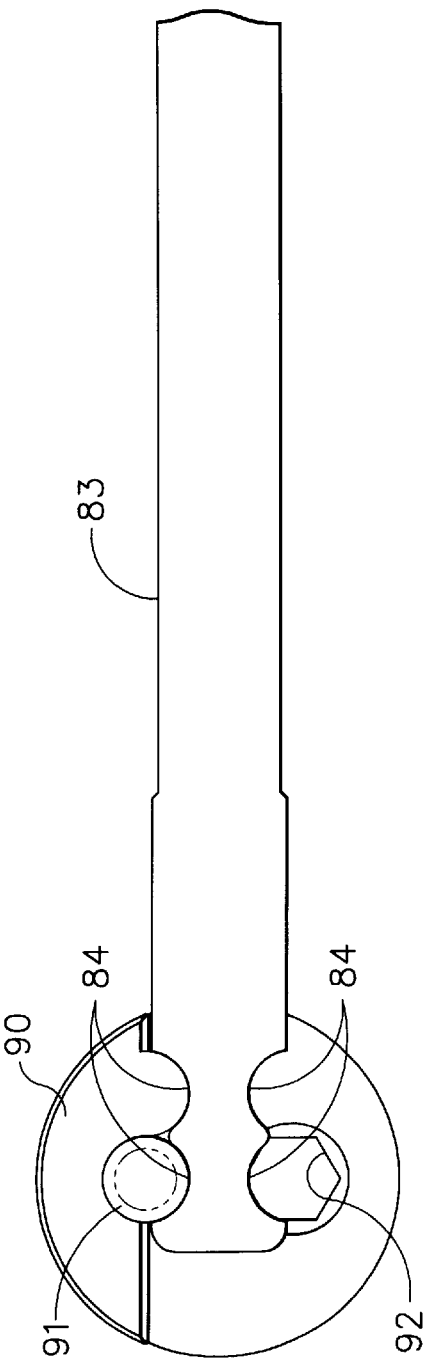
FIG. 23
FIG. 24

RATCHET RELEASE MECHANISM FOR HAND HELD INSTRUMENTS

FIELD OF THE INVENTION

The present invention relates, in general, to handheld surgical instruments and, more particularly, to a new and useful reciprocating releasable locking mechanism for locking and unlocking the actuation member of a laparoscopic hand held instrument.

BACKGROUND OF THE INVENTION

Hand held surgical instruments are well known in the surgical community and have been used for centuries. Many of these instruments have been used for grasping, dissecting, cutting, ligating, or fastening objects to the body. Of interest are hand held surgical instruments that are used to grasp or manipulate tissue during a surgical procedure. Of special interest are hand held instruments that are adapted to operate laparoscopically, that is, in a minimally invasive surgical procedure wherein the surgery is performed through a small number of small diameter surgical access ports rather than through a large opening or incision within the patient. In a typical laparoscopic surgery, the abdominal cavity is insulated with an inert gas and surgical access ports are inserted into the patient. Laparoscopic surgical instruments are inserted into the access ports and the surgical procedure is performed through these access ports. Laparoscopic surgery is sometimes referred to as "keyhole surgery" wherein the access ports are the "keyholes" through which the surgery is performed. As a consequence of the access port ("keyhole") size, laparoscopic grasping instruments are characterized by a pair of scissor-like handles, a small diameter elongated shaft that forms a gas tight seal with the access port, and an end effector that is operatively coupled with at least one of the handles.

During open and laparoscopic surgery, it is important to provide surgical instruments capable of grasping and manipulating tissue. Grasping and holding tissue over long periods of time can be tiring and can cause medical complications should the surgeon tire and lose his grip upon the tissue. It is now traditional to provide a one-way holding or clamping mechanism on surgical grasping instruments to conserve the surgeon's stamina for other surgical tasks. Many such grasping instruments use a rack and pawl clamping mechanism operatively coupled to the end effector via the scissors-like handles. The rack and the pawl have sawtooth shaped teeth that have an angled side of the tooth and an undercut side of the tooth. The rack of the grasping instrument is operatively coupled to one handle and the pawl is defectively coupled to the other. The angled side of the rack and pawl teeth are brought into sliding engagement as the end effectors are moved together to clamp on tissue and the undercut side are brought into locking engagement when the end effectors attempt to move apart. The pawl must be disengaged from the rack and the pawl must be disengaged by a cam or other means to reopen the end effectors. One such instrument for an open procedure was described by D. M. Litlejohn in U.S. Pat. No. 1,659,112. Another instrument having a pawl and a rack mechanism operably coupled to scissors-like handles was described by Bales et al. in U.S. Pat. No. 5,176,702. The instrument described by Bales et al. is used in laparoscopic surgery.

Whereas the laparoscopic graspers described by Bales et al. locked when clamped upon tissue, they were difficult to use, as they required the use of a second hand to unlock the instrument during surgery. What was needed was a laparoscopic grasping instrument having a rack and pawl locking mechanism that can be easily locked and unlocked with the same hand that actuates the instrument. Laparoscopic grasping instruments having a pair of scissors-like handles and an easily accessible trigger for unlocking the pawl from the ratchet were disclosed by Green et al. in U.S. Pat. No. 5,476,479 and by Aranyi in U.S. Pat. No. 5,483,952.

The rack and pawl locking mechanism of the laparoscopic locking instruments disclosed by Green et al. and Aranyi has a limitation. The rack and pawl mechanism does not provide infinite positions during closure but is limited to a number of discreet positions that are dependent on the distance between the rack teeth. Since the pawl must fall between two rack teeth to lock, the size of the of the rack tooth limits the number of discreet locking positions. If the tooth profile is large, the surgeon is limited to a very few discrete locking positions and the risk of clamping the tissue too tight or too loose is increased. If the tooth profile is small, the number of discreet locking positions is increased, reducing, but not eliminating, the limitations of a toothed locking mechanism.

What is needed is a locking mechanism that has an infinite number of locking positions as the handles are closed. Such a mechanism is described by T. C. Hutcheson in U.S. Pat. No. 804,229, Nicholas in U.S. Pat. No. 5,314,424, and Measamer et al. in U.S. Pat. No. 5,735,874. The locking mechanism used by Hutcheson, Nicholas, and Measamer is a plate having an aperture or hole therethrough and pivotable upon a shaft extending through the hole. The end effectors are operably coupled to the actuation handle by the shaft. When the plate is angled with respect to the longitudinal axis of the shaft, the hole becomes elliptical, contacts the shaft, and forms a one way frictional lock with the shaft. When the plate is positioned at right angles to the shaft, the actuation handle is unlocked as the hole in the plate is circular relative to the shaft and the shaft slips freely through the hole in both directions.

The inventions of Hutcheson and Measamer were indeed revolutionary, but the actuation buttons or triggers were confusing to use when actuating or unactuating the one way slip locking mechanism. The actuation mechanism for Nicholas was also confusing. What is needed is an infinitely variable one-way locking mechanism that is releasable and intuitive to use.

SUMMARY OF THE INVENTION

The present invention is a surgical instrument for grasping and clamping tissue. The surgical instrument has a handle body assembly and an elongated shaft having a proximal end and a distal end. The proximal end of the elongated shaft is connected to the handle body assembly. An end effector having at least one moveable member is located at the distal end of the shaft.

An actuation member has a proximal end, and is moveable toward and away from the handle body assembly. The actuation member is operatively connected to the end effector for actuating movement of the at least one moveable member.

A locking tab is on the handle body assembly and has a hole therethrough. The locking tab is moveable between a locked position and an unlocked position.

The present invention also includes a locking rod having a proximal end and a distal end. The locking rod is fixed to the actuation member at the proximal end of the actuation member. At least the distal end of the locking rod is moveably engaged with the locking tab through the hole when the locking tab is in the unlocked position to allow movement of the actuation member towards and away from the handle body. The locking rod is fixed relative to the locking tab when the locking tab is in the locked position to prevent movement of the actuation member away from the handle body.

A release trigger operably coupled to the locking tab is provided. The release trigger extends from the handle body and is moveable in the handle body assembly from a first position spaced away from the handle body to a second position adjacent to the handle body. The release trigger is biased toward the first position. The release trigger is reciprocable when initially squeezed toward the handle body assembly from the first position to the second position and subsequently released from the second position back to the first position. Consecutive reciprocations of the release trigger alternates the locking tab between the locked position and the unlocked position.

Significantly, the novel hand held surgical instrument for grasping and clamping tissue provides the surgeon with a releasable locking mechanism that is intuitive to use. That is, the releasable locking mechanism is locked or engaged by squeezing and releasing the release trigger and is unlocked or disengaged by resqueezing and re-releasing the release trigger. Such a mechanism is easily mastered and easily switched from locked to unlocked. Consequently, the surgeon is provided with a releasable locking mechanism that is intuitive and easy to use.

The hand held surgical instrument of the present invention provides a releasable locking mechanism that when engaged, permits unimpeded closure of the end effector and locks when the user attempts to open the end effector. This type of releasable locking mechanism is particularly adapted for grasping and clamping on tissue during open and laparoscopic surgical procedures. Such a releasable locking mechanism is ideal for surgical instruments such as graspers, Babcocks, and the like.

In particular, the hand held surgical instrument of the present invention provides a releasable locking mechanism that when engaged, provides the surgeon with an infinite number of locking positions during closure. This type of mechanism provides the surgeon with the appropriate grasping or clamping force regardless of the tissue thickness or tissue compressibility.

Additionally, the hand held surgical instrument of the present invention provides the surgeon with an ergonomic handle body assembly that is small, fits well into a surgeon's hand and is easy to operate. The ergonomic handle body assembly has an arcuate finger hook for the little finger, a central finger loop for the two center fingers, and a finger rest for the index finger. A thumb actuated moveable actuation member is provided with an actuation loop to engage the thumb. Also, the releasable locking mechanism of the hand held surgical instrument of the present invention is curved in an arcuate path to ergonomically place the release trigger relative to the index finger for easy operation and the locking tab relative to the locking rod within the handle body assembly.

Furthermore, the hand held surgical instrument of the present invention provides a universal handle body assembly for assembly with a wide variety of end effectors of different sizes, shapes and uses. Additionally, the hand held surgical instrument of the present invention provides during assembly an easily changeable stroke or displacement to actuate the end effectors. The changeable stroke is provided to better match the stroke requirements of the different end effectors.

The various features of novelty which characterize the invention are pointed out with particularity in the claims annexed to and forming a part of the disclosure. For a better understanding of the invention, reference is made to the accompanying drawings and descriptive matter in which the preferred embodiments of the invention are illustrated.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 23 is a front view of an actuation ball half-placed in a first position relative to an actuation rod of the handheld surgical instrument; and FIG. 24 is a front view of an actuation ball half-placed in a second position relative to an actuation rod of the handheld surgical instrument.

DETAILED DESCRIPTION OF THE PREFERRED EMBODIMENT OF THE INVENTION

The preferred embodiment of the present invention is a hand held surgical instrument for the grasping and clamping of tissue during a laparoscopic surgical procedure. In particular, the present invention is a laparoscopic surgical grasping and clamping instrument having a new and useful releasable locking mechanism operably attached to an end effector. When engaged, the releasable locking mechanism provides little or no resistance as the end effector is closed to grasp or clamp on tissue, and clamps or locks as the user tries to open the end effector. The locking mechanism is easily disengaged when required. The surgical instrument 30 of the preferred invention is shown in FIGS. 1–24.

Figure 1:
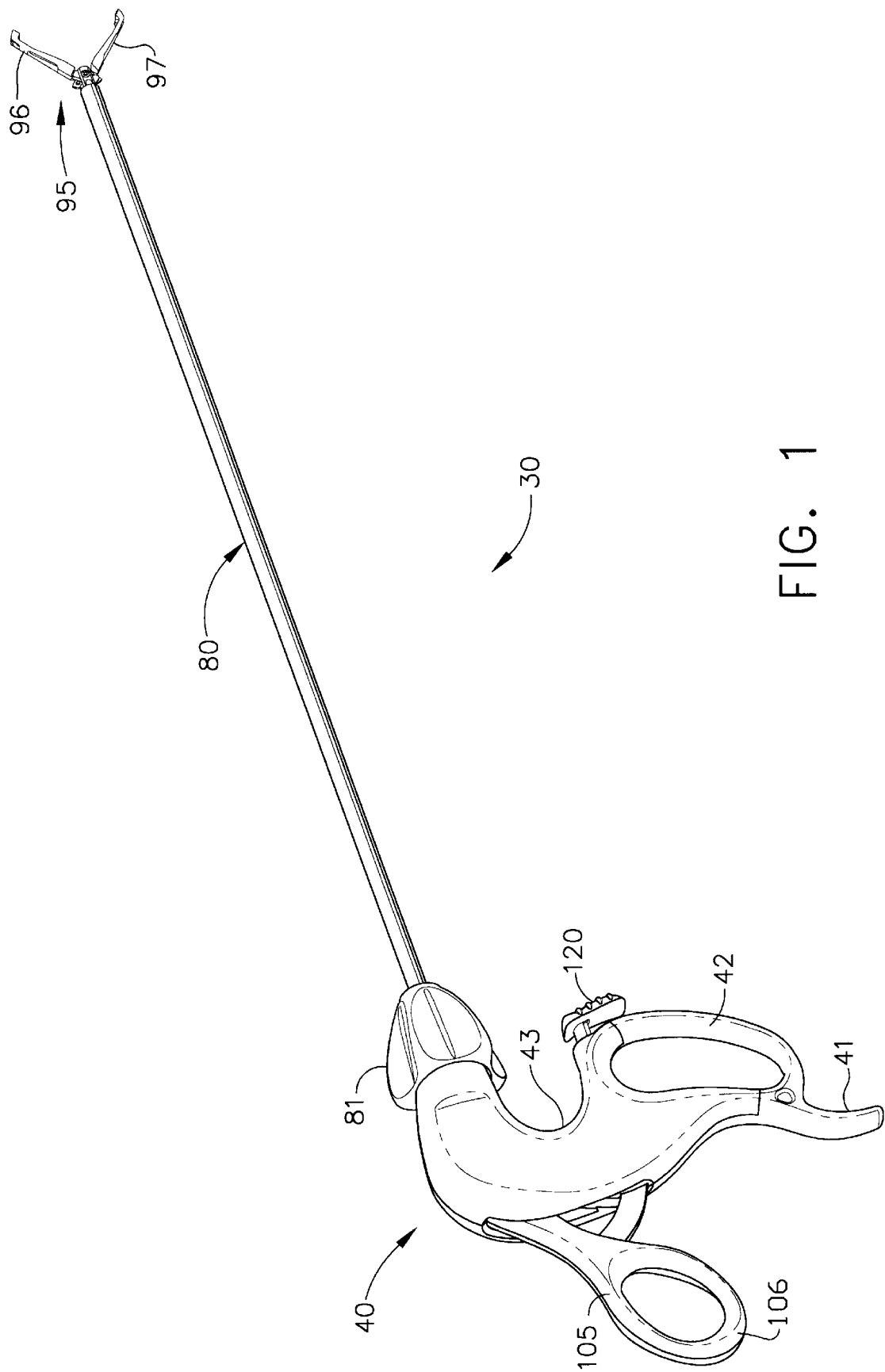
FIG. 1 is an isometric view of the preferred handheld surgical instrument of this invention having a releasable locking mechanism for locking and unlocking an actuation member of the hand held surgical instrument.

FIG. 1 shows an isometric view of the surgical instrument 30 of the preferred invention. The laparoscopic instrument has a proximal handle body assembly 40 for the surgeon to grasp, an elongated shaft assembly 80 rotatably connected to the handle body assembly 40, and an end effector 95 attached to the distal end of the elongated shaft assembly 80. It is an object of the invention to provide a universal surgical instrument that can be assembled with a wide variety of end effectors of different sizes, shapes and uses. The handle body assembly 40 is ergonomic in design having an arcuate finger hook 41 for the little finger, a fixed finger loop 42 for the two center fingers, and a finger rest 43 for the index finger. A moveable actuation member 105 has an actuation loop 106 for the thumb and is operably connected to the end effector 95. Movement of the actuation member 105 towards and away from the fixed finger loop 42 closes and opens the end effector 95. For clarity, a single pair of end effectors, first and second moveable jaw members 96 and 97 suitable for grasping and clamping tissue will be used throughout the description below. Actuation member 105 is releasably locked and unlocked by a release trigger 120 of a releasable locking mechanism 115 (FIGS. 2–3, and FIGS. 5–16). The release trigger 120 is normally biased away from the handle body assembly 40 and alternate reciprocations of the release trigger 120 towards and away from the handle body assembly 40 locks and unlocks the releasable locking mechanism 115. The majority of the releasable locking mechanism 115 is located within the handle body assembly 40 and will be described in greater detail below. The elongated shaft assembly 80 is fixably and rotatably attached within a distal end of the handle body assembly 40. A rotational knob 81 is provided to rotate the elongated shaft assembly 80 and the first and second jaw members 96 and 97.

When held in the manner described above, the laparoscopic surgical instrument 30 is easy to use and operate when grasping or clamping tissue. With the releasable locking mechanism 115 unlocked, the surgeon can easily open and close the moveable first and second jaw members 96 and 97 to grasp and manipulate tissue. To clamp the surgical instrument 30 on tissue, the surgeon opens the jaws, actuates the releasable locking mechanism 115 by reciprocating the release trigger 120 towards and away from the handle body assembly 40, and clamps or closes the moveable first and second jaw members 96 and 97 on the desired tissue. When the actuation member 105 is released, the releasable locking mechanism 115 locks and prevents the first and second jaw members 96 and 97 from opening. First and second jaw members 96 and 97 are opened by unlocking the releasable locking mechanism 115 with a second reciprocation of the release trigger 120.

Figure 2:
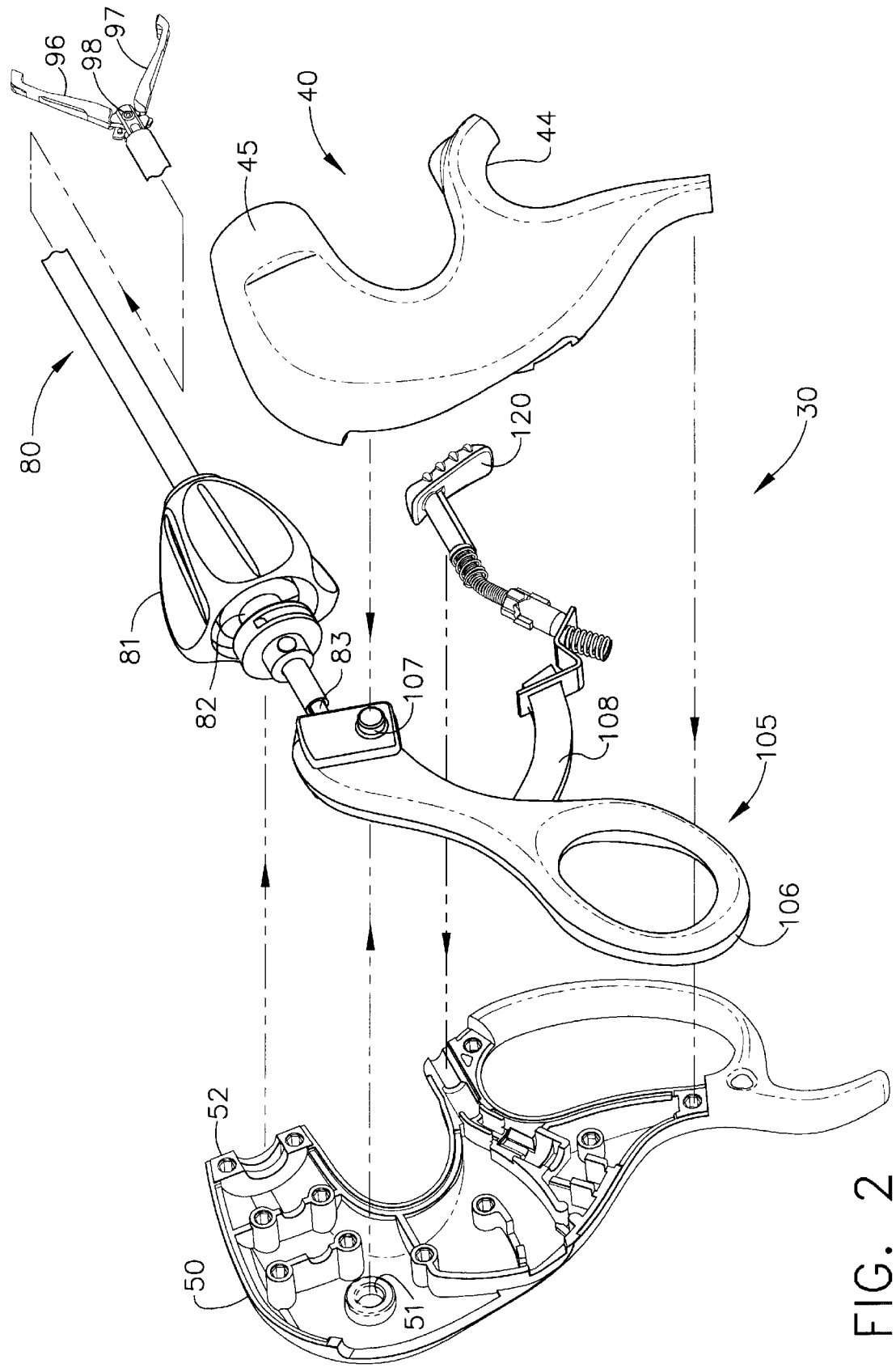
FIG. 2 is an exploded isometric view of the handheld surgical instrument of FIG. 1 showing the subassemblies that mount within a handle body assembly of the handheld surgical instrument.

FIG. 2 is an exploded isometric view of the most preferred surgical instrument of the present invention wherein a right handle cover 45 and a left handle cover 50 of the handle body assembly 40 are separated to show the elements within. The right handle cover 45 and the left handle cover 50 are generally mirror images of each other and define a longitudinal mirror plane therebetween. The exceptions to this mirror plane are generally the partial loop 44 found on the right handle cover 45, a series of gripper pins 45 (not shown) extending to the left from the interior of the right handle cover 45, and a mating series of gripper pin sockets 40a (FIG. 3) found within the left handle cover 50. Other differences will be noted. The gripper pins and the gripper pin sockets 40a are a press fit feature used to hold the handle covers together.

As shown in FIG. 2, the distal end of the left handle cover 50 has a handle flange 52 extending inwardly and the elongated shaft assembly 80 has a groove 82 near the proximal end of the rotational knob 81. The elongated shaft assembly 80 mounts within the left handle cover with the placement of the handle flange 52 within the groove 82 of the elongated shaft assembly 80. This forms a rotating coupling that longitudinally fixes the elongated shaft assembly 80 within the handle body assembly 40. The proximal end of the elongated shaft assembly 80 is rotatably and operably coupled to the actuation member 105 by an actuation rod 83. Movement of the actuation member 105 moves the actuation rod 83 proximally and distally within the elongated shaft assembly 80, and opens and closes the first and second jaw members 96 and 97.

An upper portion of the actuation member 105 has a pair of opposed pivot pins 107 extending outwardly that pivotably mount within a pair of opposed pivot bores 51 located within the right and left handle covers 45 and 50. The actuation member 105 pivotably mounts within the handle covers 45 and 50 with the placement of the pivot pins 107 into the pivot bores 51. An arcuate locking rod 108 of rectangular cross section extends distally from the actuation loop 106 of the actuation member 105. It is of note that the arcuate locking rod 108 (as well as the rest of the actuation member 105) is made from an engineering thermoplastic such as styrene, polycarbonate, polyetheramid, liquid crystal polymer, or any other of a number of engineering thermoplastics commonly used for medical instruments.

The releasable locking mechanism 115 (including release trigger 120) is shown assembled and operably coupled to the locking rod 108 of the actuation member 105 for the locking and unlocking of the actuation member 105, and indirectly the first and second jaw members 96 and 97. The releasable locking mechanism 115 alternately engages and disengages the actuation member 105 in response to consecutive reciprocations of the release trigger 120 towards and away from the handle body assembly 40 and will be described in greater detail below.

Figure 3:
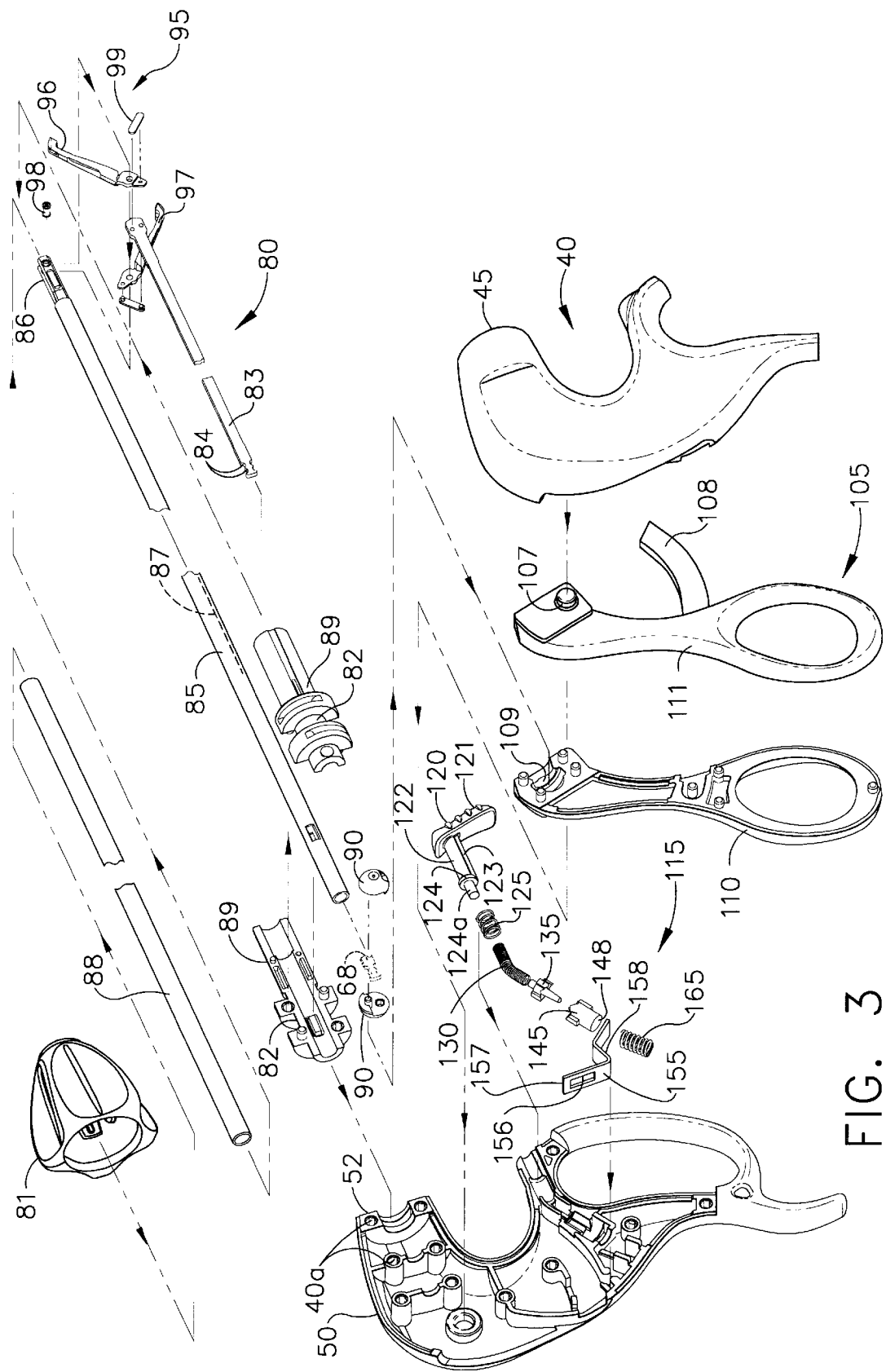
FIG. 3 is an exploded isometric view showing all of the elements of the handheld surgical instrument of FIG. 2 in exploded form.

FIG. 3 is an isometric view showing all of the components of FIG. 2 in exploded form. The backbone of the elongated shaft assembly 80 is an elongated shaft 85 formed from a thin sheet of surgical grade metal. The elongated shaft 85 is not formed in the conventional manner wherein a stainless steel tube is fabricated to form elongated shaft 85, but is formed from a flat sheet in a series of forming dies such as a progressive stamping and forming die. The flat sheet of steel is curled or formed into a hollow elongated shaft 85 having a cylindrical cross section, a longitudinal seam 87, and a distal clevis 86. The longitudinal seam 87 is where the longitudinal edges of the flat strip of steel (not shown) are curled together to form a cylindrical elongated shaft 85. The stamping and forming process is such that the longitudinal edges are brought into preloaded contact with one another and the longitudinal seam 87 is not shown as it is located upon the bottom of the elongated shaft 85 in FIG. 3. Insulation material 88 is applied over the elongated shaft 85 to protect the surgeon and the patient during the use of electrocautery. A pair of shaft adapters 89 that engage with a proximal end of the elongated shaft 85 are locked together by the rotational knob 81. The shaft adapters 89 have the groove 82 mentioned above for the capture of the handle flange 52 when the elongated shaft assembly 80 is installed into the handle body assembly 40. At the distal end of the elongated shaft 85, a pivot member 98 moveably attaches the first and second jaw members 96 and 97 within clevis 86.

The actuation rod 83 is coaxialy located and moveable within elongated shaft 85. A pair of links 99 of the end effector 95 operatively connects the distal end of actuation rod 83 to the first and second jaw members 96 and 97. Two pairs of opposed notches 84 are located at the proximal end of the actuation rod 83, one pair proximally and one pair distally. The reader is advised that the sectioned proximal end of the actuation rod 83 appears twice in the exploded view of FIG. 3 to provide clarity on the method of assembly. A pair of actuation ball halves 90 attach to one of the pairs of notches 84 to provide a ball shaped rotation and actuation coupling at the distal end of the actuation rod 83 (see FIGS. 23–24). Each of the actuation ball halves 90 have a locking pin 91 and a locking socket 92 and are pressed together to form a ball. It is important during assembly to position the ball halves 90 to align the locking pins 91 with opposing locking sockets 92. As shown in FIGS. 23 and 24, the actuation ball half 90 can be locked in one of two positions—within the proximal or distal pair of notches 84. FIG. 23 shows the proximal attachment position and FIG. 24 shows the distal attachment position prior to the attachment of the second actuation ball half 90. This two position attachment of the actuation ball half 90 provides two different strokes or linear outputs at the end effector 95. The dual stroke feature is especially desirable during manufacturing where it is a goal to use common handle body assembly 40 and elongated shaft assembly 80 parts with many different sizes and styles of end effectors, some with different stroke requirements.

The assembled actuation ball halves 90 form a ball shaped rotation and actuation coupling that mounts within a ball socket 109 that is located inside a left member half 110 and a right member half 111 of the actuation member 105. The left member half 110 and the right member half 111 lock together to capture the assembled actuation ball halves 90 within the assembled actuation member 105.

As shown in exploded form in FIG. 3, the releasable locking mechanism 115 consists of the release trigger 120, a trigger spring 125, a flexible member 130, a cam button 135, a plunger 145, a locking tab 155, and a locking tab spring 165. The release trigger 120, the trigger spring 125, the transmission member 125, and the cam button 135 connect together to form a sub-assembly. The elements of the releasable locking mechanism 115 mount within the right handle cover 45 and the left handle cover 50 of the handle body assembly 40.

The release trigger 120 of FIG. 3 is generally "T" shaped and reciprocally mounts within the handle body assembly 40. Consecutive reciprocation of the release trigger 120 towards and away from the handle body assembly 40 engages and disengages the releasable locking mechanism 115. Release trigger 120 has a distal finger pad 121 for engagement with a finger (not shown) and a distally extending trigger shaft 122. A rib 123 extends longitudinally on the bottom of trigger shaft 122 resulting in a keyhole shaped shaft that prevents rotation of the finger pad 121 in the handle body assembly 40. A retention ring 124 is also provided at the proximal end of the trigger shaft 122 to engage with the trigger spring 125 and to prevent expulsion of the release trigger 120 from the handle body assembly 40. A pin 124*a* (Figure) extends proximally from the retention ring 124 and fixably attaches to the flexible member 130 at the proximal end of the release trigger 120.

The flexible member 130 is a tightly coiled spring that transmits force and motion inputs from the release trigger 120 to the other moving elements of the releasable locking mechanism 115 in an arcuate path. It is obvious to one skilled in the art that a number of other transmission members such as a flexible tube, a thin wire, a string of beads, or any one of a number of flexible transmission members will likewise transmit force and motion in an arcuate path.

Figure 21:
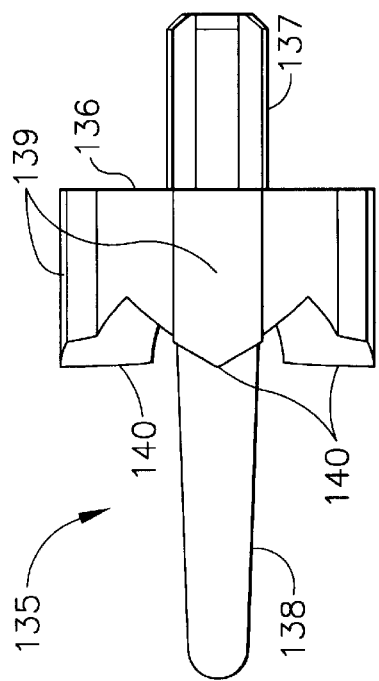
FIG. 21 is a top view of the cam button of FIG. 20 of the handheld surgical instrument.
Figure 20:
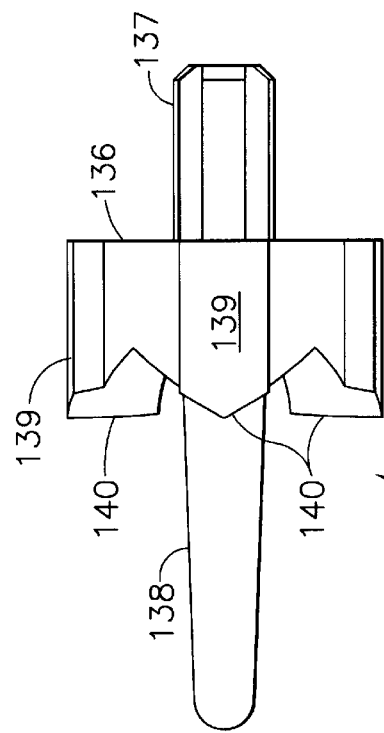
FIG. 20 is a front view of a cam button of the handheld surgical instrument.
Figure 22:
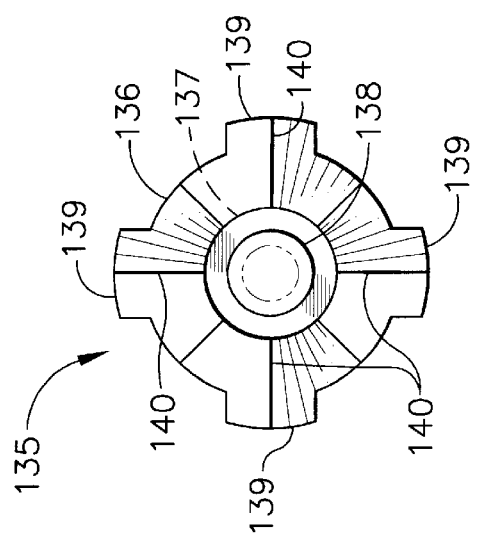
FIG. 22 is an end view of a cam button of FIG. 21 of the handheld surgical instrument.

The cam button 135 of FIG. 3 is coupled to a distal end of flexible member 130 and reciprocates proximally and distally within the handle body assembly 40. Cam button 135 is best shown in FIGS. 20–22 and engages with the plunger 145 to lock and unlock the releasable locking mechanism 115. The cam button 135 has a central button shaped disk 136, a proximal post 137 that attaches to the flexible member 130, and a distal guide shaft 138. Four equally spaced cam ribs 139 extend radially outwardly from the disk 136 to prevent rotation of the cam button 135 within the handle body assembly 40. Four cam teeth 140 are located on a proximal face of the cam button 135 and extend radially inwardly from each cam rib 139. The use of these cam teeth 140 will be described later. The guide shaft 138 extends proximally from the cam teeth 140 to align and guide the plunger 145.

Figure 19:
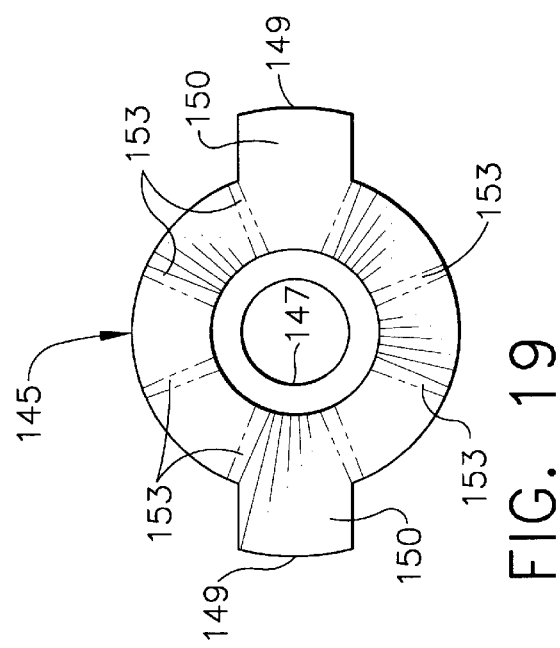
FIG. 19 is an end view of a plunger of FIG. 17 of the handheld surgical instrument.
Figure 18:
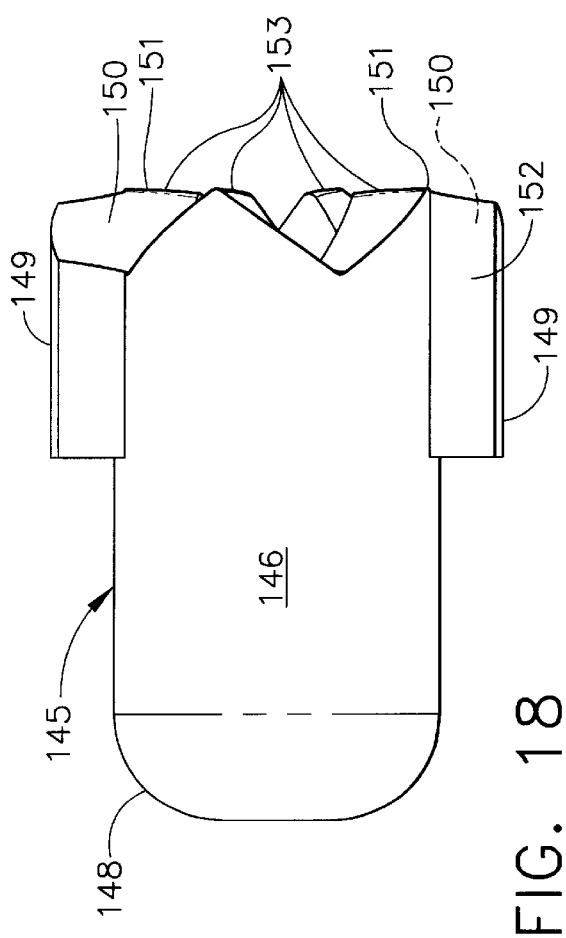
FIG. 18 is a top view of the plunger of FIG. 17 of the handheld surgical instrument.
Figure 17:
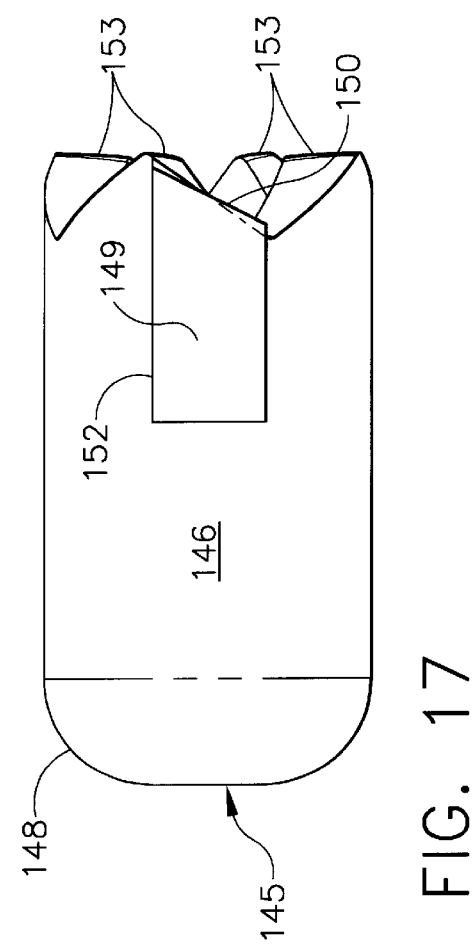
FIG. 17 is a front view of a plunger of the handheld surgical instrument of FIG. 1.

The plunger 145 of FIG. 3 reciprocates and rotates throughout a number of positions within the handle body assembly 40 for the locking and unlocking of the releasable locking mechanism 115. As best shown in FIGS. 17–19, plunger 145 is generally a hollow cylinder having a body 146 and a bore 147 (FIG. 19) for the reception of the guide shaft 138 therein. A pair of opposed plunger ribs 149 extend radially outwardly near the distal end of the body 146. An inclined ramp surface 150 is located at the distal end of each plunger rib 149 for engagement with features of the right handle cover 45 and the left handle cover 50. The inclined ramp surfaces 150 and a peak face 152 forms a plunger peak 151 at the distal end of each plunger rib 149. Four equally spaced plunger teeth 153 of the same size and pitch as the four cam teeth 140 (FIG. 20) of the cam button 135 are located on a distal face of the body 146 and extend radially inwardly. It is of note that the plunger ribs 149 are not in direct alignment with the plunger teeth 153 and the significance of this will be noted below. The use of this inclined ramp surface 150 and the plunger teeth 153 in locking and the unlocking the actuation member 105 will be described in detail below. A rounded face 148 is located at the proximal end of the plunger 145 for engagement with the locking tab 155.

The locking tab 155 of FIG. 3 pivotably mounts within the right handle cover 45 and the left handle cover 50 and engages the rectangular locking rod 108 of the actuation member 105. Locking tab 155 is a flat strip of material formed into a "Z" shape and having a rectangular locking hole 156 within a vertical leg 157 for the reception of the locking rod 108. An upper and a lower surface within the locking hole 156 are smooth to grip or clamp the locking rod 108 at any position. The locking rod 108 freely slides within locking tab 155 when the locking tab 155 is pivoted to a position generally perpendicular to a tangent line drawn at the point of contact. When the locking tab 155 is pivoted to an appropriate angle it frictionally locks with the locking rod 108 in one direction and slidably engages with the locking tab 155 in the opposite direction. In the orientation shown in FIG. 14, the locking tab 155 will lock with the locking rod 108 as the actuation member 105 tries to move away from the handle body assembly 40. The locking tab 155 is normally biased towards the rounded face 148 of the plunger 145 and towards the locked position by the locking tab spring 165. It is the position of the plunger 145 relative to the handle body assembly 40 that locks and unlocks the locking tab 155 with the locking rod 108.

Figure 4:
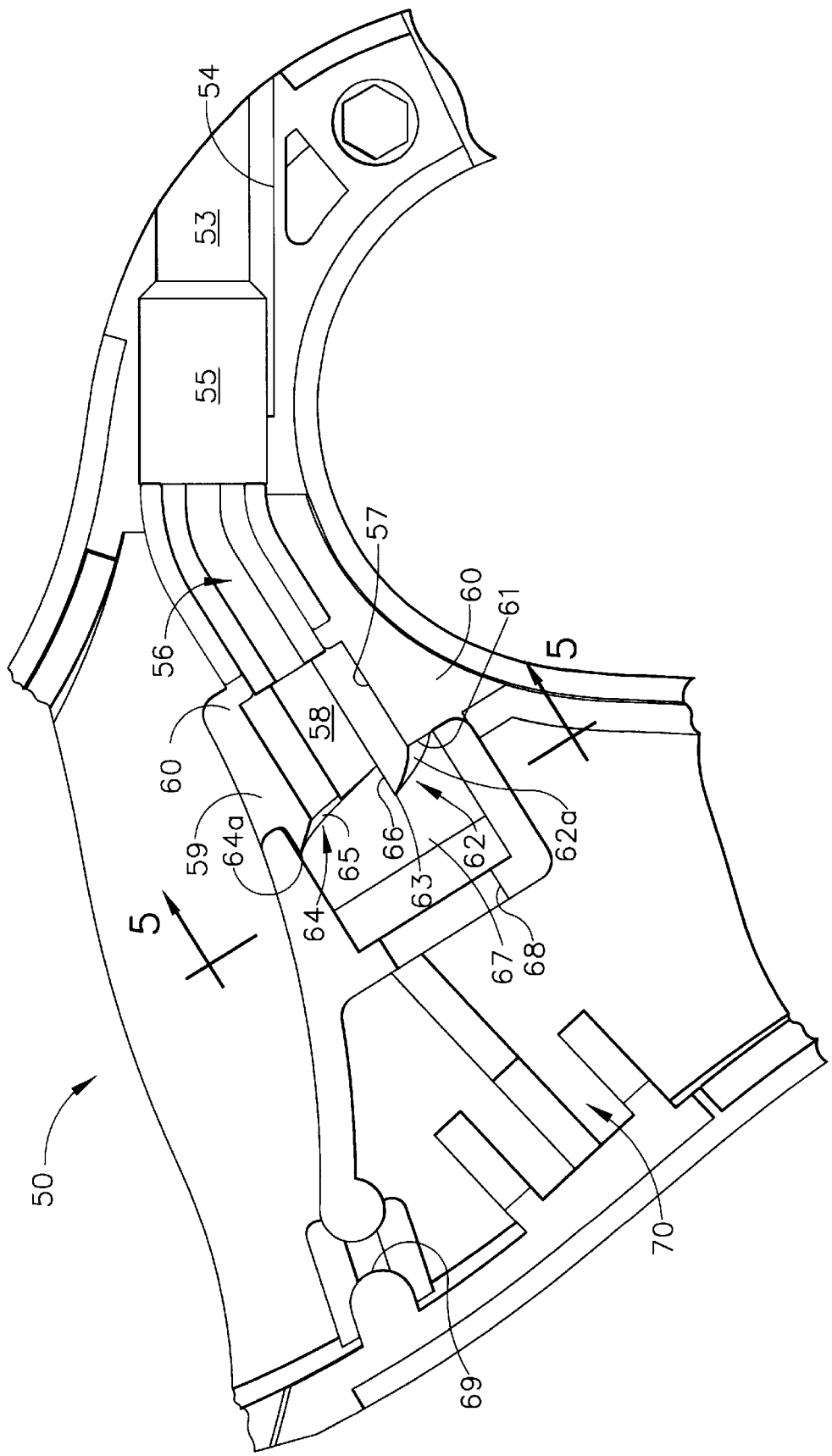
FIG. 4 is a side view of a portion of the interior of a left handle cover of the handle body assembly showing features that hold and engage the releasable locking mechanism of the handheld surgical instrument of FIG. 1.

FIG. 4 is an enlarged view of the inner features of the left handle cover 50 that hold and operably engage with the moveable elements of the releasable locking mechanism 115. The moveable elements of releasable locking mechanism 115 mount in an arcuate path within these inner features which, for the most part, are mirrored in the right handle cover 45 (FIG. 3). When the left handle cover 50 and the right handle cover 45 are assembled, the inner features that hold the elements of releasable locking mechanism 115 generally form an arcuate series of interconnecting cylinders or slots within the central portion of the handle body assembly 40. The generally cylindrical features of the arcuate path of the releasable locking mechanism 115 are, for the most part equally split longitudinally between the right handle cover 45 and the left handle cover 50.

A trigger bore 53 and a trigger slot 54 is located above the fixed finger loop 42 of the left handle cover 50. Trigger bore 53 and the trigger slot 54 forms a keyhole shaped opening within handle body assembly 40 for the reception of the release trigger 120 and rib 123 (FIG. 3). The keyhole shaped opening prevents rotation of the keyhole shaped trigger shaft 122 and rib 123. A cylindrical trigger spring bore 55 having a diameter larger than the trigger bore 53 is located Coaxially with and proximally to the trigger bore 53. The trigger spring 125 (FIG. 3) and the proximal end of release trigger 120 mounts within the cylindrical trigger spring bore 55 to bias the release trigger 120 away from the handle body assembly 40 (see arrow in FIG. 6). An arcuate slot 56 extends proximally from the trigger spring bore 55 for the reception and guidance of the flexible member 130 (FIG. 3).

Figure 5:
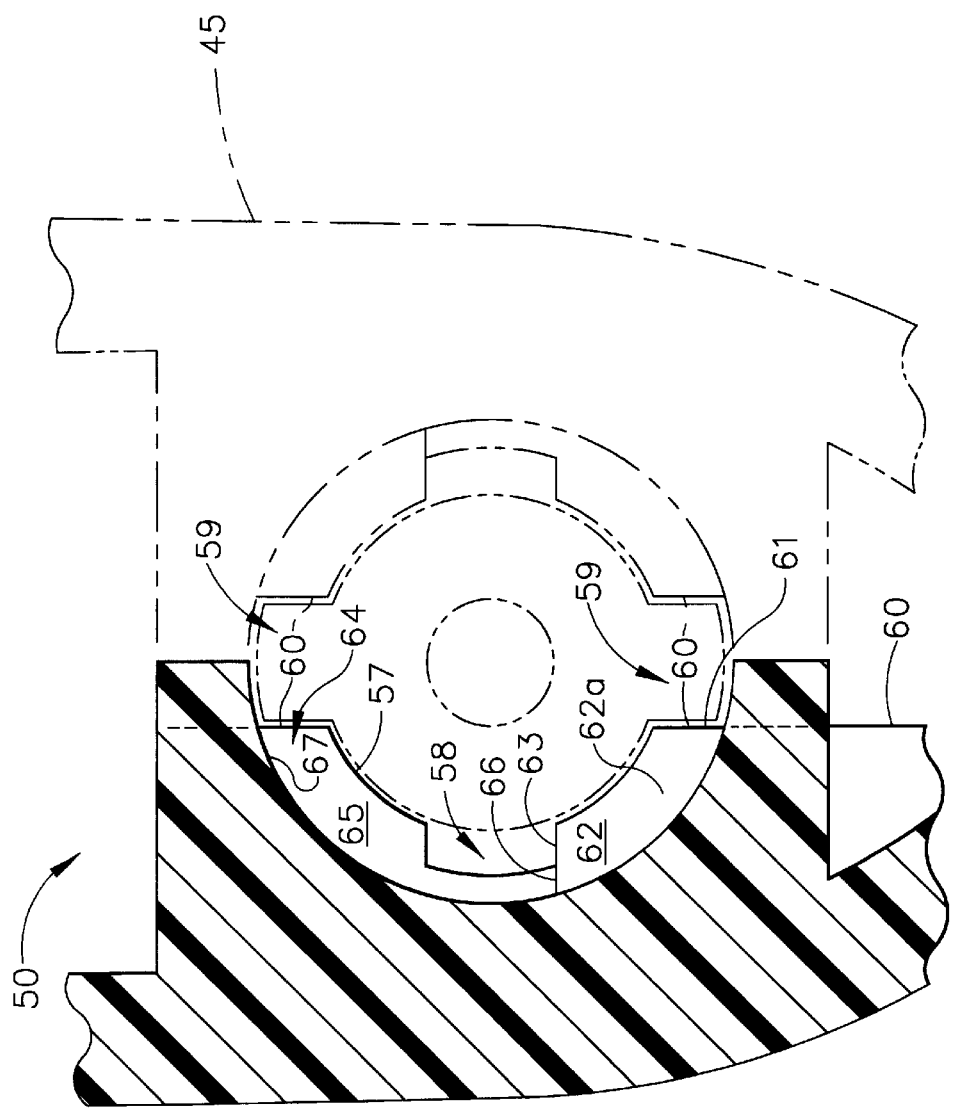
FIG. 5 is a section view of a portion of the left handle cover in crosshatch and a portion of the right handle cover in phantom lines.

The proximal end of the arcuate slot 56 connects to a cylindrical cam button bore 57. The cam button bore 57 receives the reciprocating cam button 135. A pair of horizontal slots 58 and a pair of vertical slots 59 radiate outwardly from the longitudinal axis of cam button bore 57 into the right handle cover 45 and the left handle cover 50. The horizontal slots 58 and the vertical slots 59 receive the cam ribs 139 of the cam button 135 and prevent the cam button 135 from rotating as it reciprocates. The cam button bore 57 and vertical slots 59 are equally split along the vertical longitudinal axis between the left handle cover 50 and the right handle cover 45 as shown in FIG. 5. A single horizontal slot 58 is located in the left handle cover 50 and an opposing horizontal slot is mirrored in the right handle c over 45. The reader is advised to note a pair of vertical surfaces 60 that defines the left and the right walls of the vertical slots 59, one in the right handle cover 45 and one in the left handle cover 50.

In FIG. 4, the distal end of the cam button bore 57, the horizontal slots 58, a nd the vertical slots 59 open into a larger cylindrical plunger bore 67. FIG. 5 is provided to show a cross section of the left handle cover 50 across the plunger bore 67. The plunger bore 67 of the handle body assembly 40 has a pair of locking teeth 62 and a pair of unlocking teeth 64 extending distally from between each pair of horizontal and vertical slots 58 and 59. The locking teeth 62 and the unlocking teeth 64 alternate around the plunger bore 67 as best shown in FIG. 5. In FIG. 4, the locking tooth 62 and the unlocking tooth 64 within the left handle cover 50 have two different tooth profiles. These tooth profiles play a significant role in alternately locking and unlocking the releasable locking mechanism 115.

As shown in FIG. 4, the profile of the locking tooth 62 is formed from a stop surface 66 that extends from the horizontal slot 58 and an angled locking ramp 62a. The stop surface 66 and locking ramp 62a intersect at a locking peak 63. The locking ramp 62a extends at an angle (FIG. 4) from the locking peak 63 to intersect with the vertical surface 60 (of vertical slot 59) at a locking edge 61. The profile of the unlocking tooth 64 is formed from an unlocking ramp 65 extending at a shallow angle from stop surface 66 and the wall of the plunger bore 67 (FIG. 4). In each right and left handle cover 45 and 50, the unlocking ramp 65 (FIG. 4) intersects with the vertical surface 60 at an unlocking edge 64a. The purpose of these features will be described later. A cylindrical journal 68 is provided at a proximal end of the plunger bore 67 for the reception of the plunger 145.

A locking tab slot 69 is located above and proximal to the cylindrical journal 68 within the left handle cover 50 for the reception of the locking tab 155 (FIG. 3). The locking tab slot 69 is mirrored within the right handle cover 45 (not shown). A spring pocket 70 is provided below the locking tab slot 69 for the reception of the locking tab spring 165. The locking tab spring 165 normally biases the locking tab 155 towards the locked position and against the rounded face 148 of the plunger 145.

The assembly, placement, and operation of the elements of the releasable locking mechanism 115 will now be described in some detail. The reader is advised to turn to FIG. 3 for the exploded view showing the individual elements of the releasable locking mechanism 115, to FIGS. 11–16 for additional details of the cam button 135 and plunger 145, and to FIG. 4 for features of the handle covers that hold and interact with the elements of the releasable locking mechanism 115. The right handle cover 45 is removed in FIGS. 6, 8, 10, 12, 14, and 15 to show the placement of the internal elements within. In section views in FIGS. 5, 7, 9, 11, 13, and 16, the sectioned left handle cover 50 is shown in crosshatch, and the right handle cover 45 is shown in phantom lines.

Figure 6:
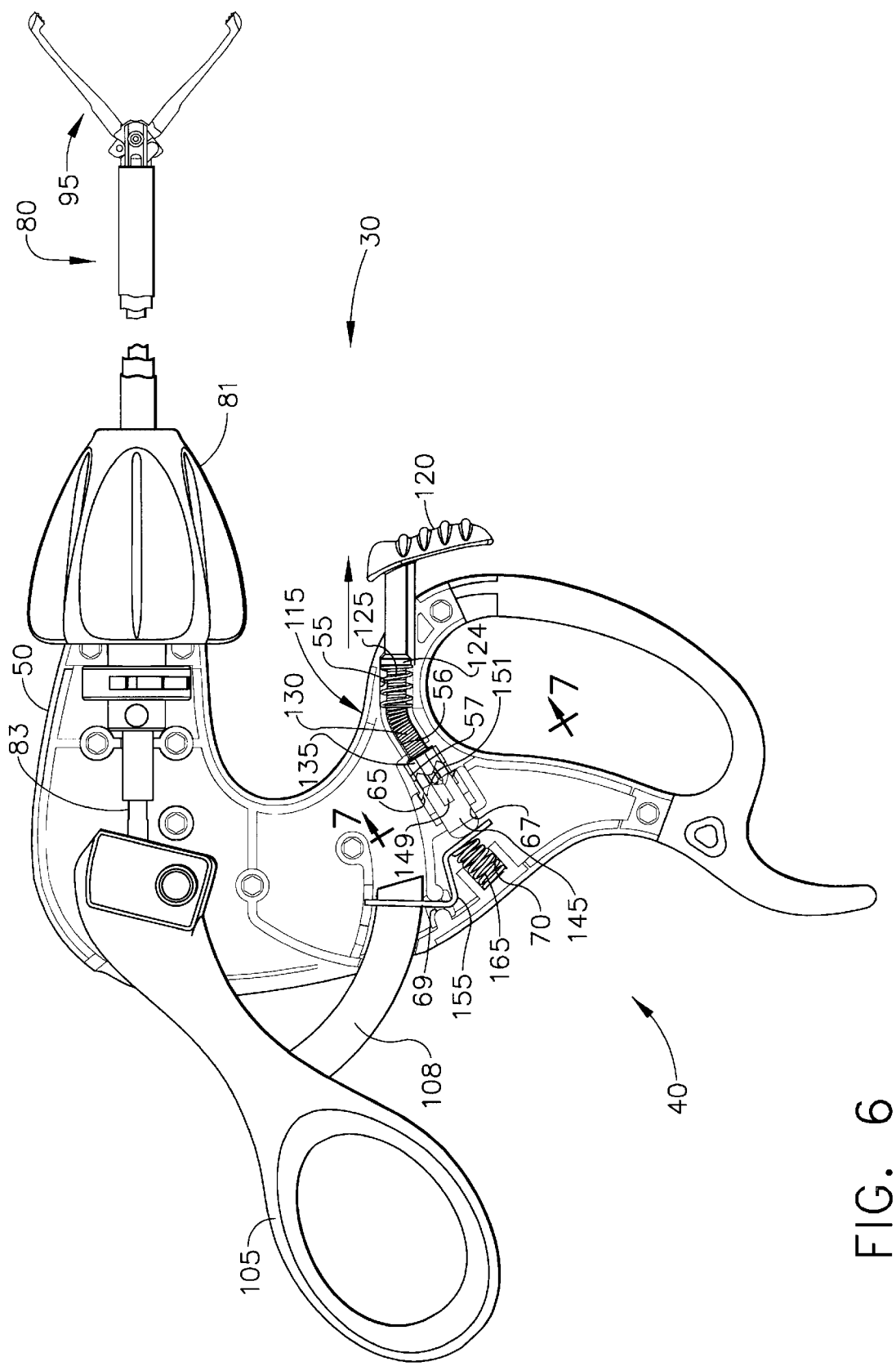
FIG. 6 is side view of the assembled handheld surgical instrument of FIG. 1 with the right cover removed to show the position of the elements when the releasable locking mechanism is unlocked.

The assembled surgical instrument 30 in FIG. 6 shows the releasable locking mechanism 115 in the unlocked position wherein the actuation member 105 is free to move. Actuation member 105 is shown moved away from the handle body assembly 40 to open the end effector 95. Reciprocating release trigger 120 is biased to the normal position away from the handle body assembly 40 by the trigger spring 125. The retention ring 124 is biased against a distal end of the trigger spring bore 55 and prevents the expulsion of the release trigger 120. An arrow is provided above the release trigger 120 to indicate the direction of the bias.

Figure 7:
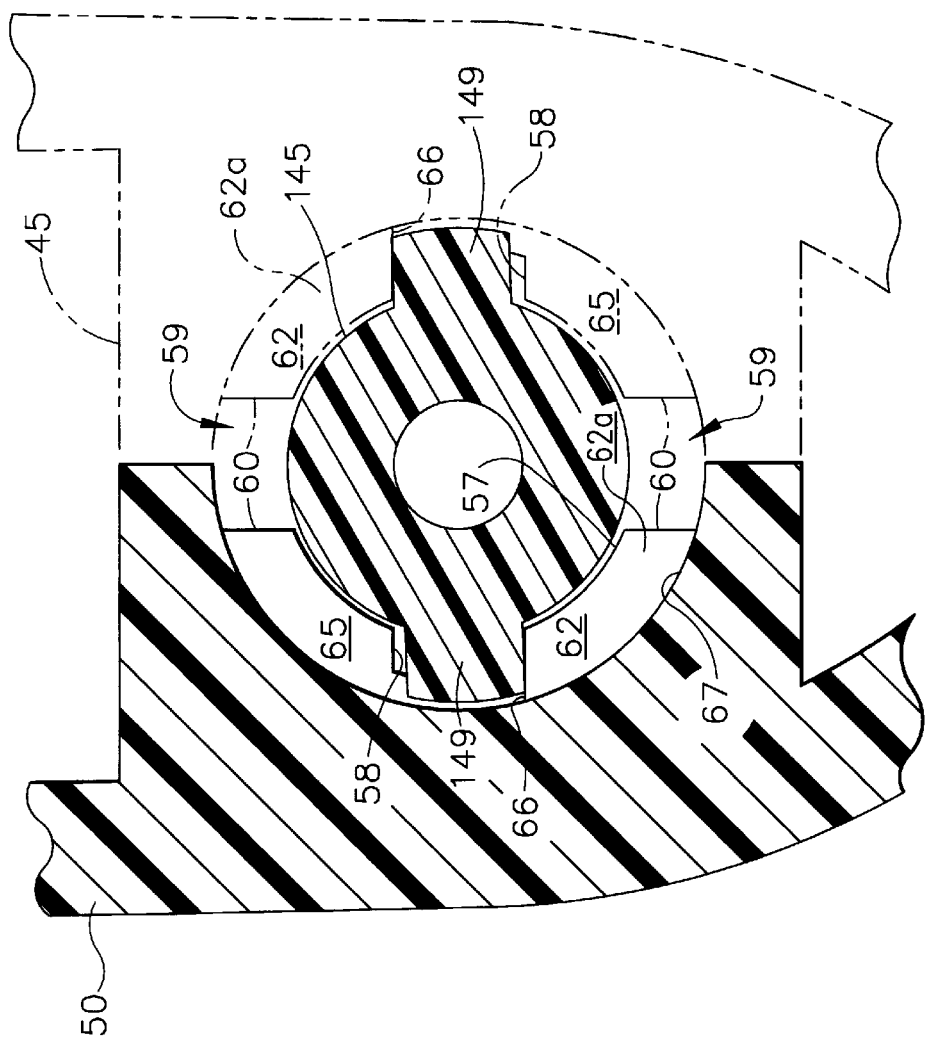
FIG. 7 is a section view of a portion of the assembled handheld surgical instrument of FIG. 6 showing the position of a plunger relative to the crosshatched left handle cover and the phantom lined right handle cover when the releasable locking mechanism is unlocked.

Release trigger 120 and cam button 135 are operably connected by the flexible member 130 which reciprocates in the arcuate slot 56 of the left handle cover 50. The releasable locking mechanism 115 is in the unlocked position and cam button 135 is biased against the distal end of the cam button bore 57 by the trigger spring 125. The cam button 135 is prevented from rotating by the capture of the cam ribs 139 within the horizontal slots 58 and the vertical slots 59 of the right and left handle covers 45 and 50. The plunger 145 is shown captured within the plunger bore 67 in an unlocked position spaced proximally away from the cam button 135. This unlocked position has the plunger ribs 149 of the plunger 145 in a generally horizontal orientation. The plunger 145 is biased distally by the locking tab spring 165 and the locking tab 155 and the distal plunger peaks 151 of the plunger ribs 149 are captured within a pair of horizontally opposed valleys formed from the intersection of the stop surfaces 66 (FIG. 4) and the unlocking ramps 65 (FIG. 4). FIG. 7 is also provided to show a sectioned view of the plunger 145 and the plunger bore 67 to emphasize the capture of both of the plunger peaks 151 within both of the valleys formed by stop surfaces 66 and the unlocking ramps 65.

As shown in FIG. 6 the locking tab 155 is pivotably mounted within the locking tab slot 69 within the left handle cover and is shown in the unlocked position. The locking tab 155 is oriented vertically within the handle body assembly 40 by the locking rod 108 passing through the locking hole 156. Locking tab spring 165 constantly biases the pivoting locking tab 155 distally against the reciprocating plunger 145. As noted above, it is the position of the plunger 145 (relative to the handle body assembly 40) that engages or disengages the locking tab 155 with the locking rod 108. The locking tab spring 165 is shown within the spring pocket 70 of the left handle cover 50.

Figure 8:
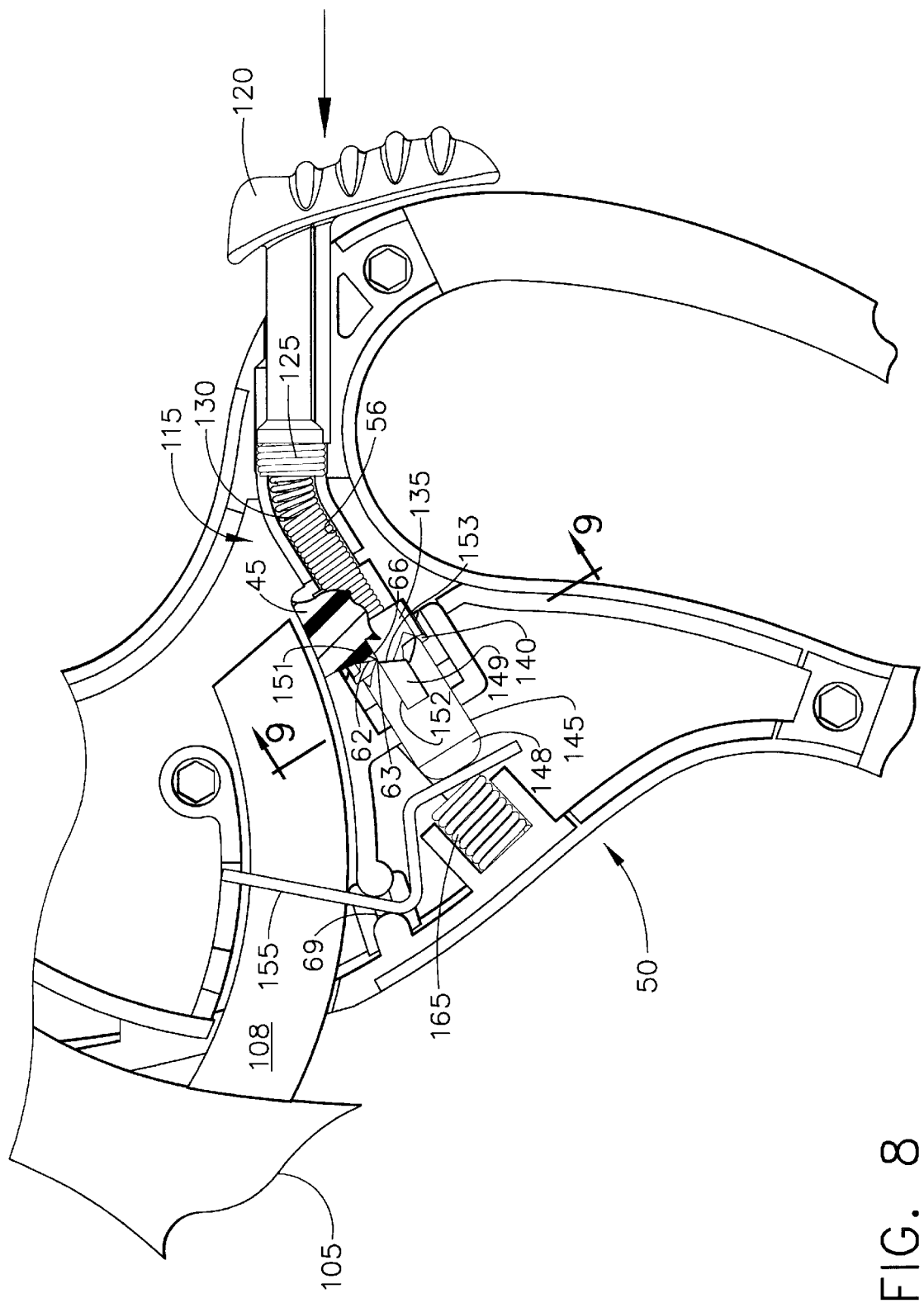
FIG. 8 is a side view of the assembled handheld surgical instrument of FIG. 1 with the right cover removed to show a first position of the elements when the releasable locking mechanism is in the process of becoming locked.
Figure 9:
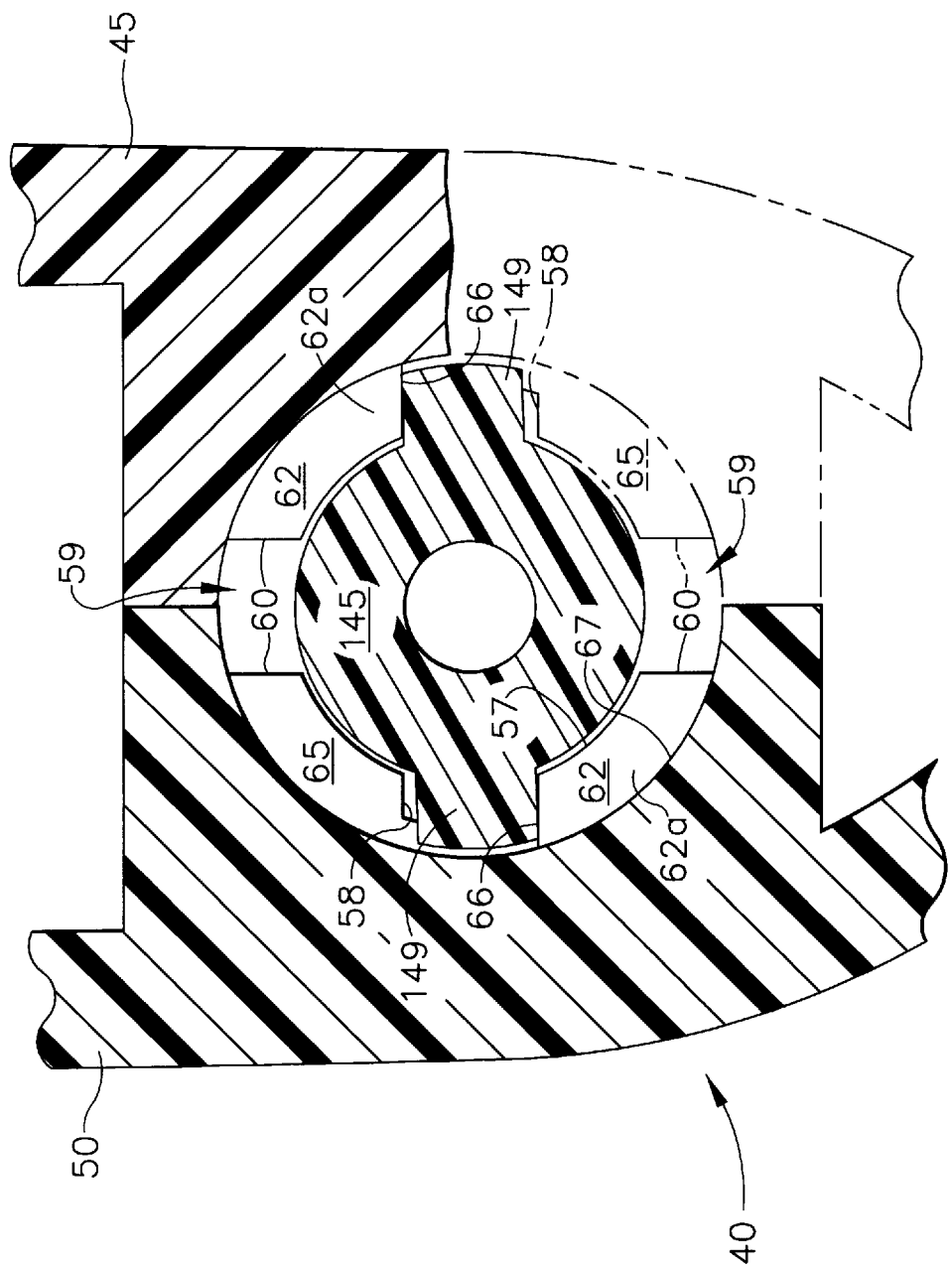
FIG. 9 is a section view of a portion of the assembled handheld surgical instrument of FIG. 1 showing the position of the plunger relative to the crosshatched left handle cover and the phantom lined right handle cover when the releasable locking mechanism is in the process of becoming locked.

FIGS. 8 to 14 illustrate the process of switching the releasable locking mechanism 115 from the locked position to the unlocked position with a first reciprocation of the release trigger 120. FIG. 8 is similar to that of FIG. 6 but shows the releasable trigger 120 partially squeezed in a first step of the process of switching the releasable locking mechanism 115 from the unlocked position to the locked position. FIG. 9 provides a cross section of a portion of FIG. 8 showing the orientation of plunger 145 with the features of plunger bore 67. In FIG. 8 the release trigger 120 is shown partially squeezed and compressing the trigger spring 125 in the direction of motion indicated by the arrow. The flexible member 130 has transferred the force and motion from the release trigger 120 in an arcuate path within the arcuate slot 56 to move the cam button 135 proximally within the cam button bore 57 and into contact with the plunger 145. This motion has moved the plunger 145 distally to the position wherein the plunger peaks 151 (at the distal ends of the plunger ribs 149) are poised to pass the locking peaks 63 of the locking teeth 62. A small sectioned portion of the locking peak 63 of the right handle cover 45 is shown in cross hatch in FIG. 8 to clearly show the positions of the plunger peaks 151 relative to the locking peaks 63.

It is also of note that the cam teeth 140 are not fully engaged with the plunger teeth 153 as the cam button 135 moves the plunger 145 distally. This partial tooth engagement is caused by the fixed orientation of the cam teeth 140 relative to the handle body assembly 50 and the rotational orientation of the plunger 145 as shown in FIGS. 8 and 9. The rotational orientation of the plunger 145 is caused by the contact of the peak faces 152 of the plunger ribs 149 with the stop surfaces 66 of the right and the left handle covers 45 and 50. The locking tab 155 is unlocked with the locking rod 108 in the position shown in FIG. 8.

Figure 10:
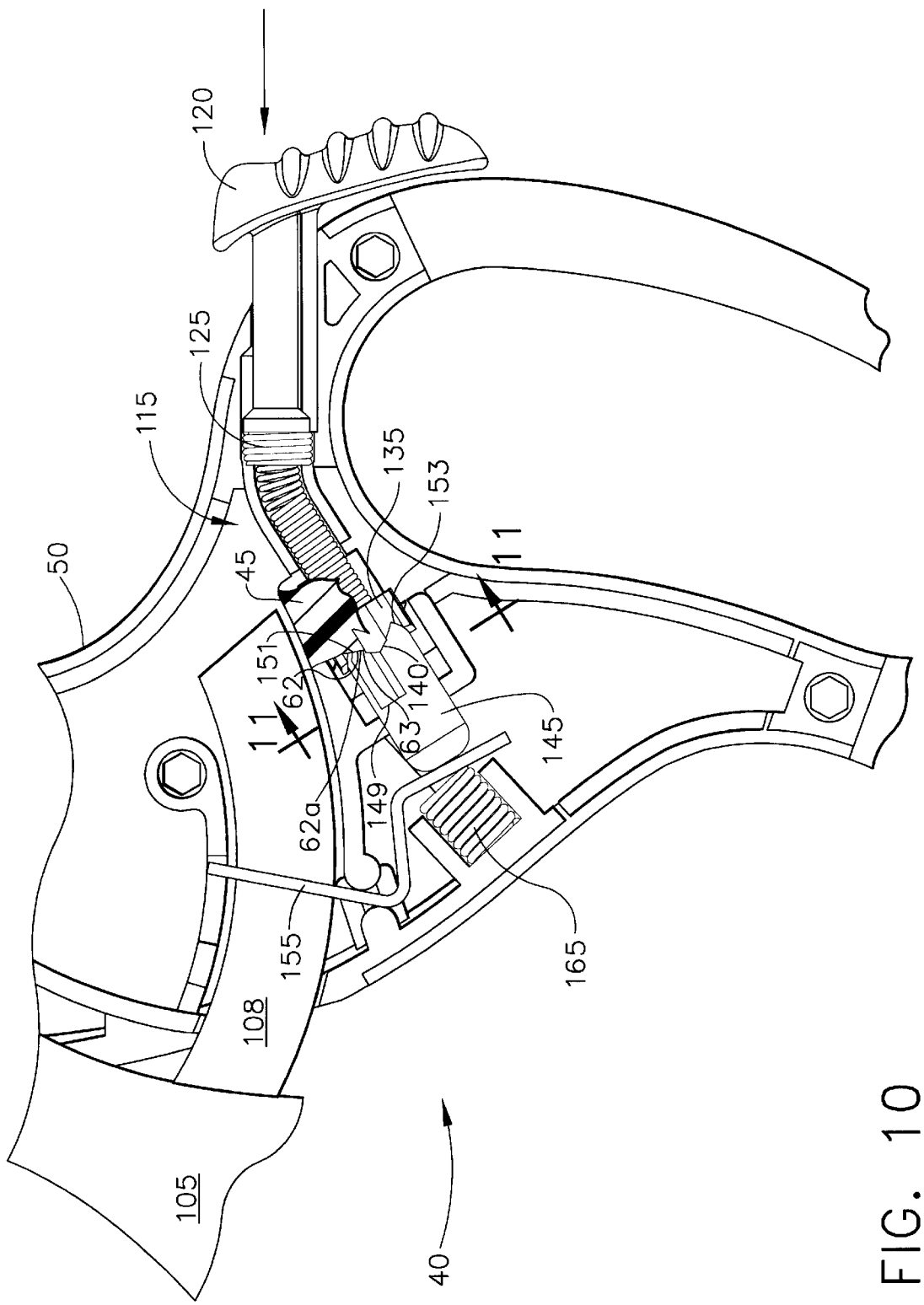
FIG. 10 is a side view of the assembled handheld surgical instrument of FIG. 1 with the right cover removed to show a second position of the elements when the releasable locking mechanism is in the process of becoming locked.
Figure 11:
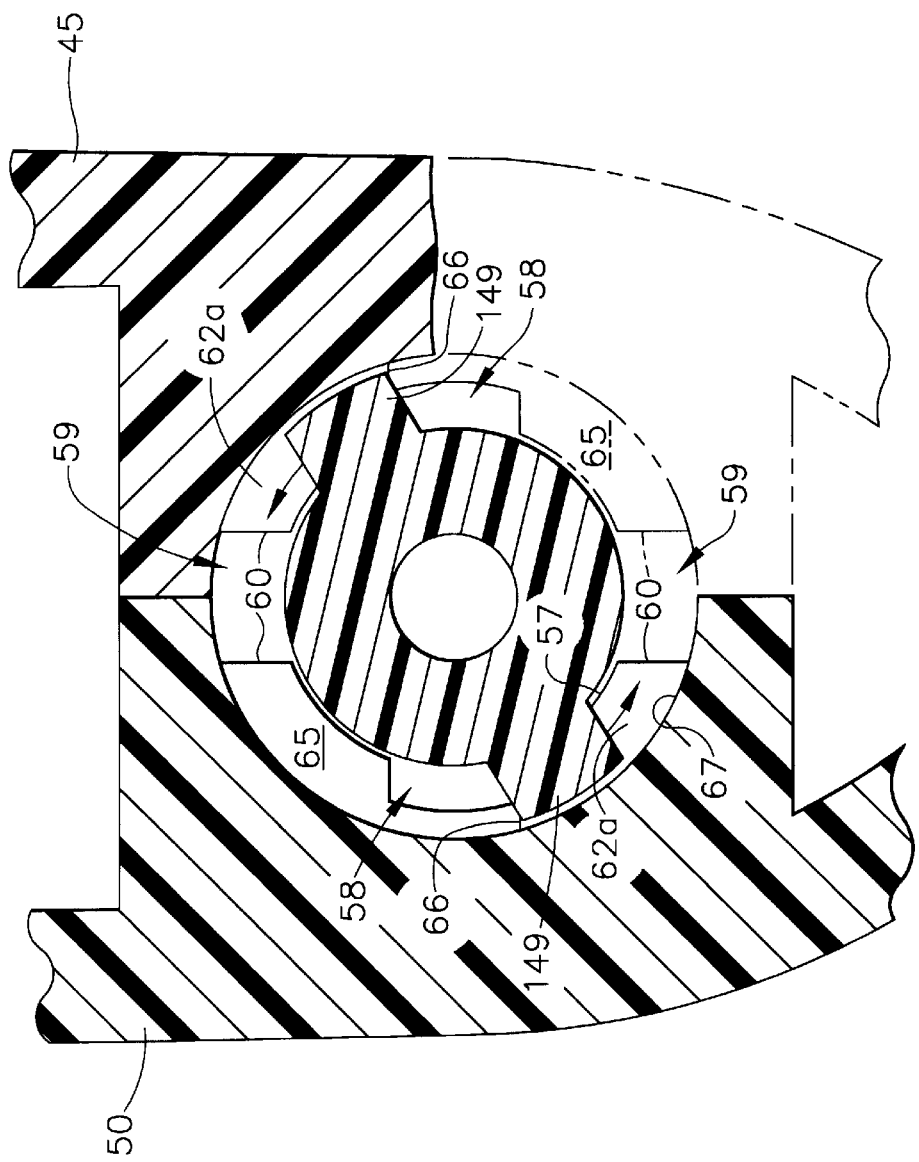
FIG. 11 is a section view of a portion of the assembled handheld surgical instrument of FIG. 1 to show the position of the plunger relative to the crosshatched left handle cover and the phantom lined right handle cover when the releasable locking mechanism is in the process of becoming locked.

FIG. 10 is similar to that of FIG. 8 but shows the elements of the releasable locking mechanism 115 in a second step in the process of switching from unlocked to locked. In FIG. 10, the continuing proximal movement of the release trigger 120 has moved the plunger peaks 151 of the plunger 145 distally past the locking peaks 63 of the right and left handle covers 45 and 50 thus freeing the plunger 145 to rotate. With the plunger 145 free to rotate, the distal bias of the compressed locking tab spring 165 has forced the partially engaged plunger teeth 153 of FIG. 8 to slide down the cam teeth 140 of the cam button 135 to the position shown in FIG. 10. This sliding motion moves the plunger 145 distally and rotates the plunger 145 (see arrow generally pointing up) past the locking peaks 63 to the position shown in FIGS. 10 and 11. Once the cam teeth 140 and the plunger teeth 153 are fully engaged, the plunger 145 reverses direction and moves proximally along with the cam button 135 until the release trigger 120 bottoms against the right and left handle covers 45 and 50 (not shown). At this point both the trigger spring 125 and the locking tab spring 165 are fully compressed. As the release trigger 120 is released, the elements of the releasable locking mechanism 115 move to the right under the bias of the locking tab spring 165 and the trigger spring 125 back to the position shown in FIGS. 10 and 11. At this point the plunger peaks 151 re-engage with the locking ramps 62a of the right and left handle covers 45 and 50. A small sectioned portion of the locking tooth 62 of the right handle cover 45 is provided to clearly show the engagement of the plunger peaks 151 of the plunger 145 with the locking ramps 62a.

Figure 12:
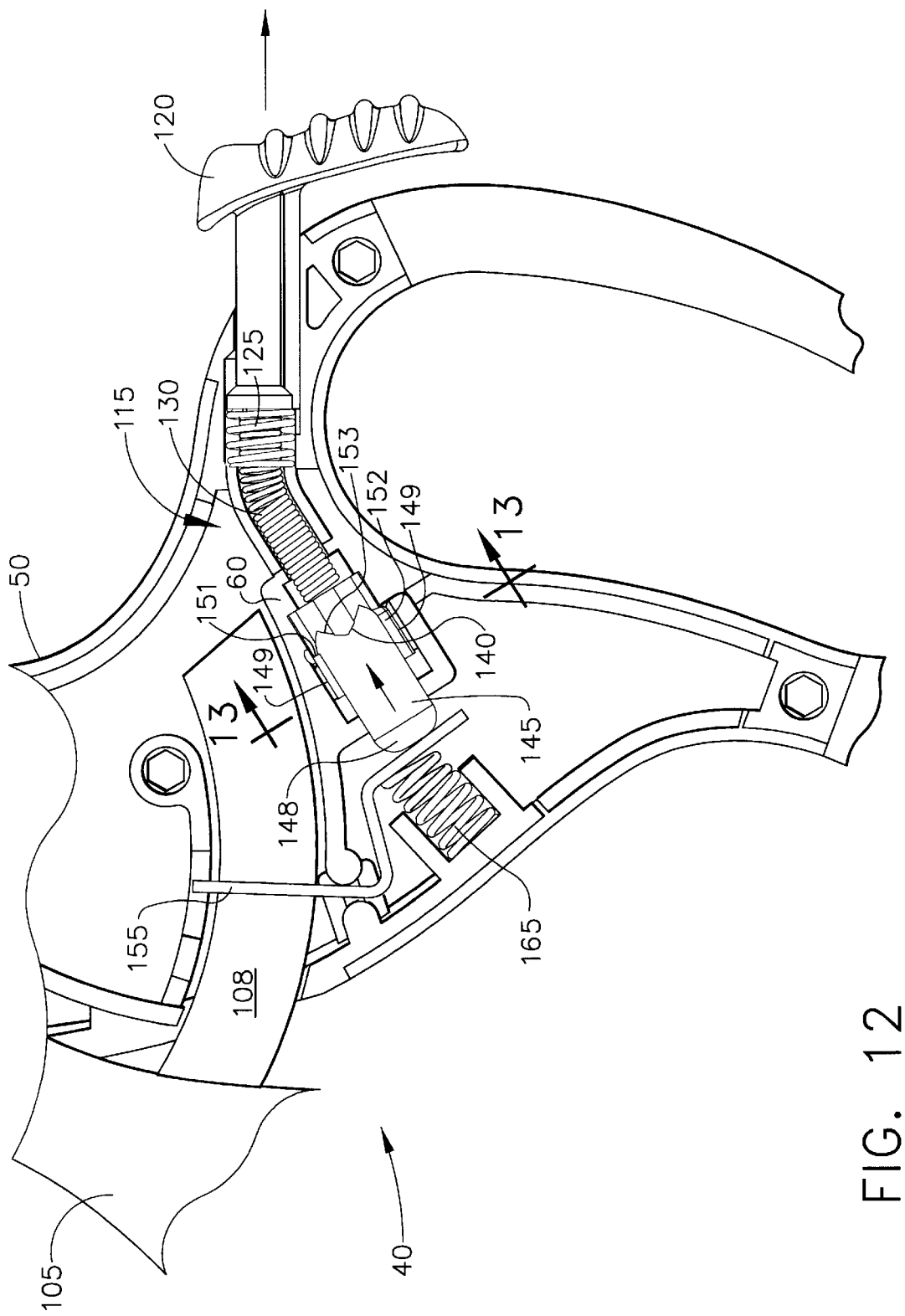
FIG. 12 is a side view of the assembled handheld surgical instrument of FIG. 1 with the right cover removed to show a third position of the elements when the releasable locking mechanism is in the process of becoming locked.

The cam button 135 and plunger 145 continue to move distally from the second position shown in FIG. 10 towards the third position shown in FIG. 12. It is the contact of the plunger peaks 151 with the locking ramp 62a that rotates the plunger 145 to the position shown in FIG. 12. An arrow is shown above the plunger 145 to indicate direction of rotation. As the plunger 145 rotates from the position of FIG. 10, the plunger teeth 153 slide on the cam teeth 140 and separate the plunger 145 from the distally moving cam button 135. The separation enables the plunger teeth 153 to ride up one side of a first set of cam teeth 140 and jump into engagement with the next set of cam teeth 140. This jump and rotation moves the plunger 145 into the position shown in FIG. 12.

Figure 13:
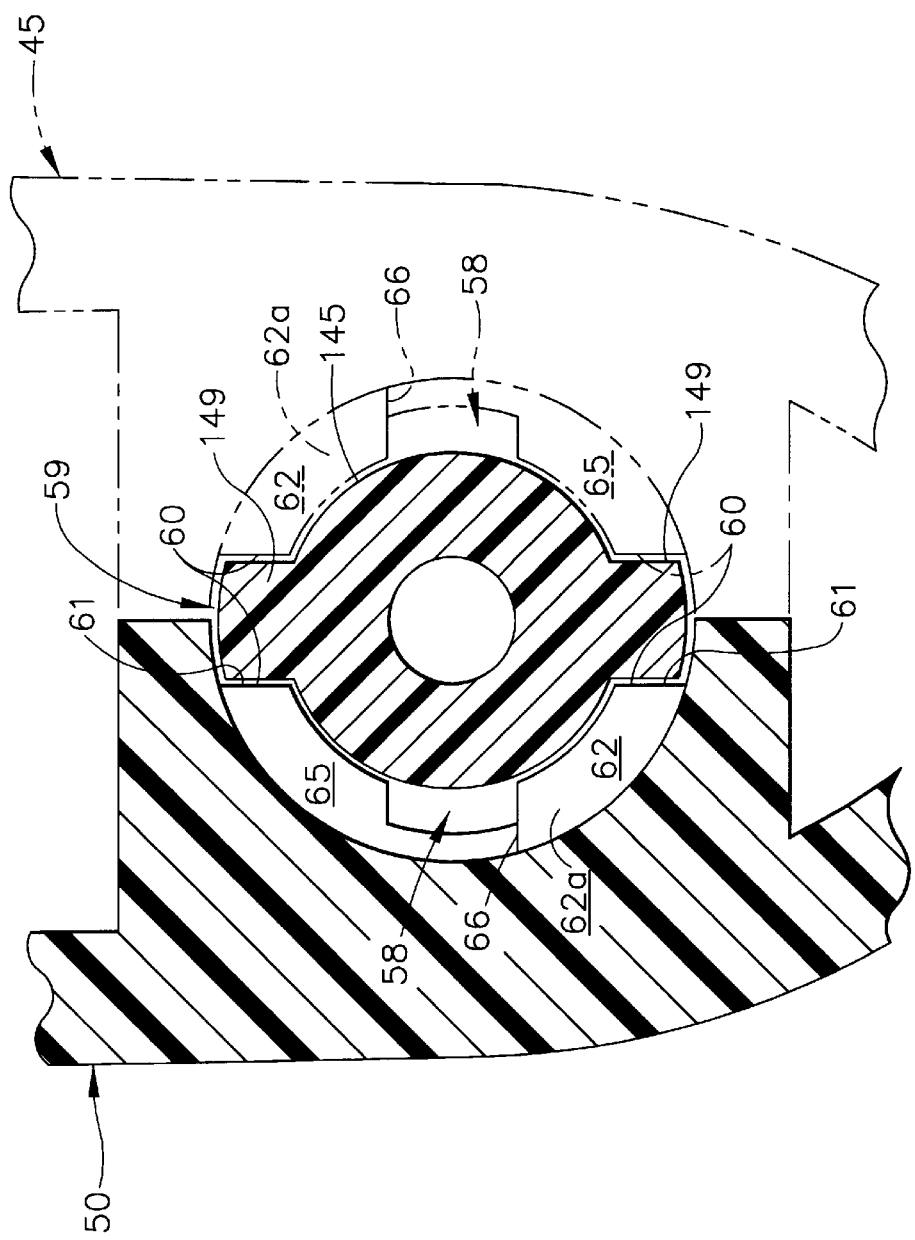
FIG. 13 is a section view of a portion of the assembled handheld surgical instrument of FIG. 1 showing the position of the plunger relative to the crosshatched left handle cover and the phantom lined right handle cover when the releasable locking mechanism is in the process of becoming locked.

In FIGS. 12 and 13, the plunger ribs 149 of the plunger 145 are in alignment with the vertical slots 59 of the right and left handle covers 45 and 50. The plunger 145 is constrained from further rotation by the contact of the peak faces 152 (FIGS. 17–19) of the plunger ribs 149 with the vertical surfaces 60 of the right and left handle covers 45 and 50. In this position, the plunger 145 is free to move distally under the bias of the partially compressed locking tab spring 165 into the vertical slots 59 and complete the unlocking process. The bias of the locking tab spring 165 also forces the plunger teeth 153 into partial engagement with the cam teeth 140. The cam teeth 140 and the plunger teeth 153 remain partially engaged as long as the plunger ribs 149 of the plunger 145 are within the vertical slots 59.

Figure 14:
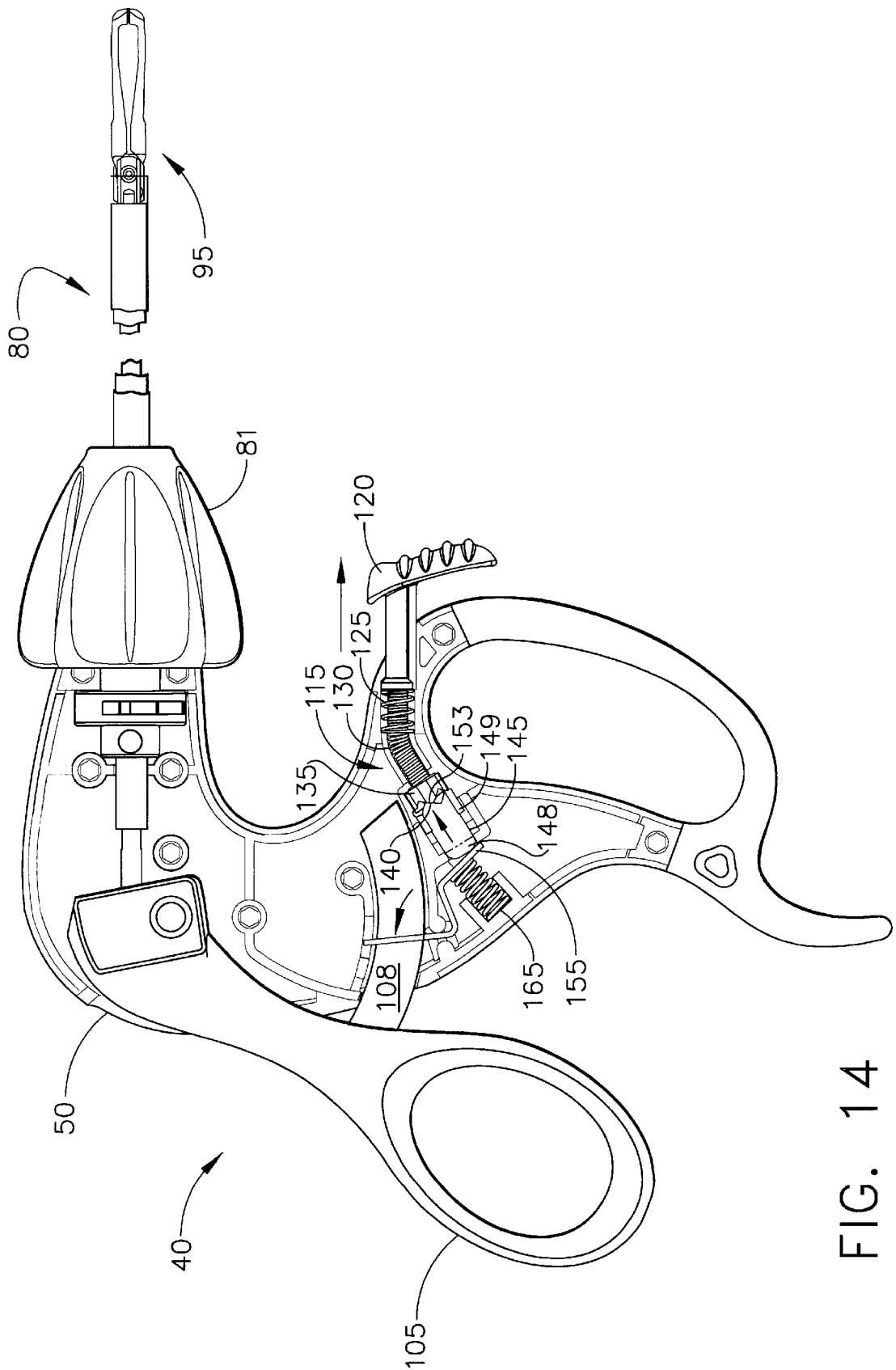
FIG. 14 is a side view of the assembled handheld surgical instrument of FIG. 1 with the right cover removed to show the elements when the releasable locking mechanism is locked.

In FIG. 14, the elements of the releasable locking mechanism 115 have completed their distal motion and the surgical instrument 30 is shown with the releasable locking mechanism 115 in the locked position. The release trigger 120 is back in the normal position (fully extended away from the handle body assembly 40) and has completed one full reciprocation to lock the releasable locking mechanism 115. That is, the release trigger 120 has moved from the normal extended position of FIG. 6, to a position adjacent or against the right and left handle covers 45 and 50, and back to the position shown in FIG. 14. The end effector 95 is in the fully closed position and the releasable locking mechanism 115 will lock when the attempt is made to open the end effector 95. Opening the closed actuation member 105 is now impossible without an additional reciprocation of the release trigger 120 to disengage the releasable locking mechanism 115.

The locking tab 155 is shown in locked engagement with the locking rod 108. The locking tab 155 and the plunger 145 are biased distally by the locking tab spring 165 and the plunger 145 has moved to the distal most position enabling the locking tab 155 to rotate counterclockwise to the locked position (see arrow). The trigger spring 125 is biasing the release trigger 120 to the extended position shown in FIG. 14. The elements of the releasable locking mechanism 115 will remain in the locked position until the actuation member 105 is reciprocated a second time.

Figure 15:
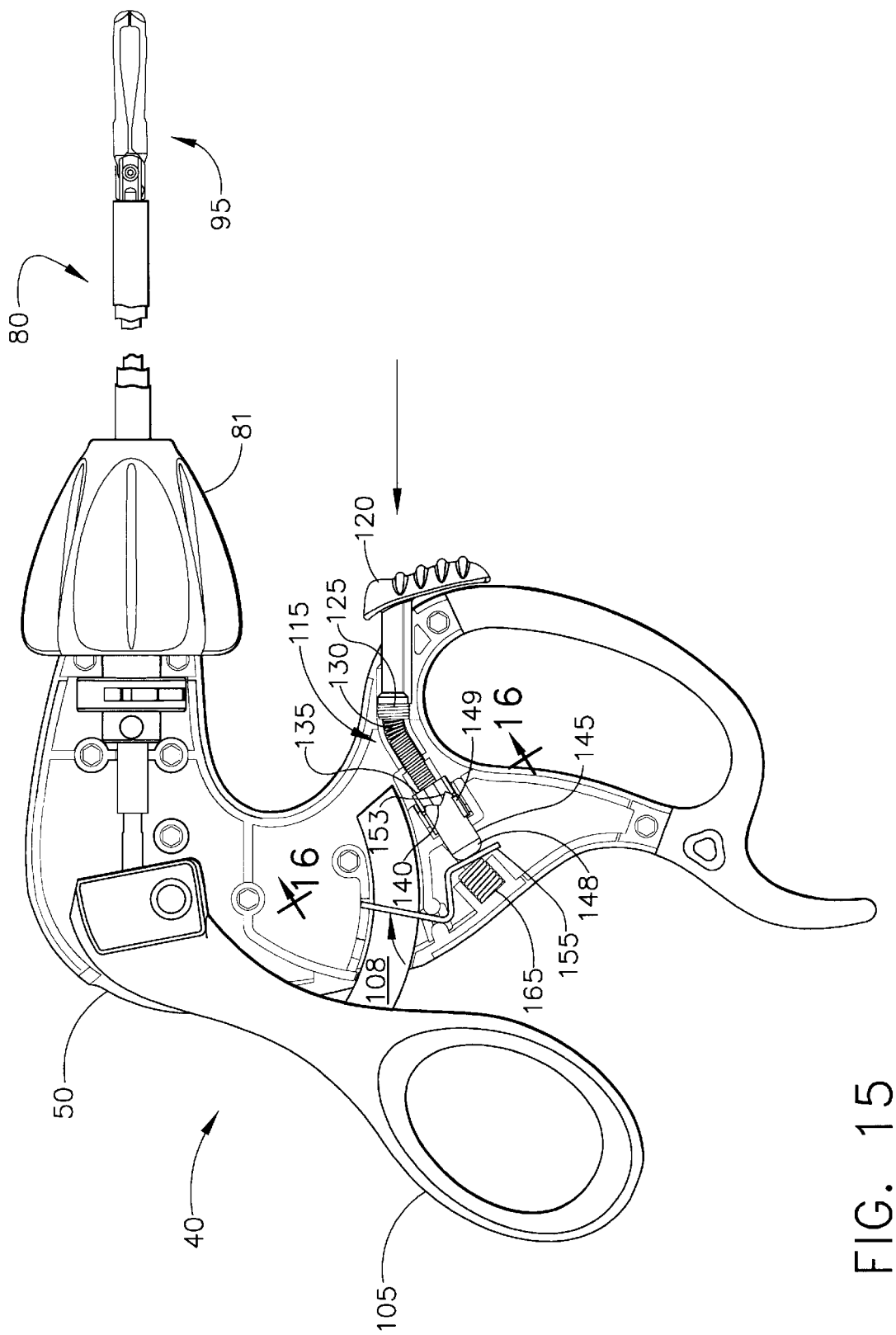
FIG. 15 is a side view of the assembled handheld surgical instrument of FIG. 1 with the right cover removed to show the elements when the releasable locking mechanism is in the process of becoming unlocked.
Figure 16:
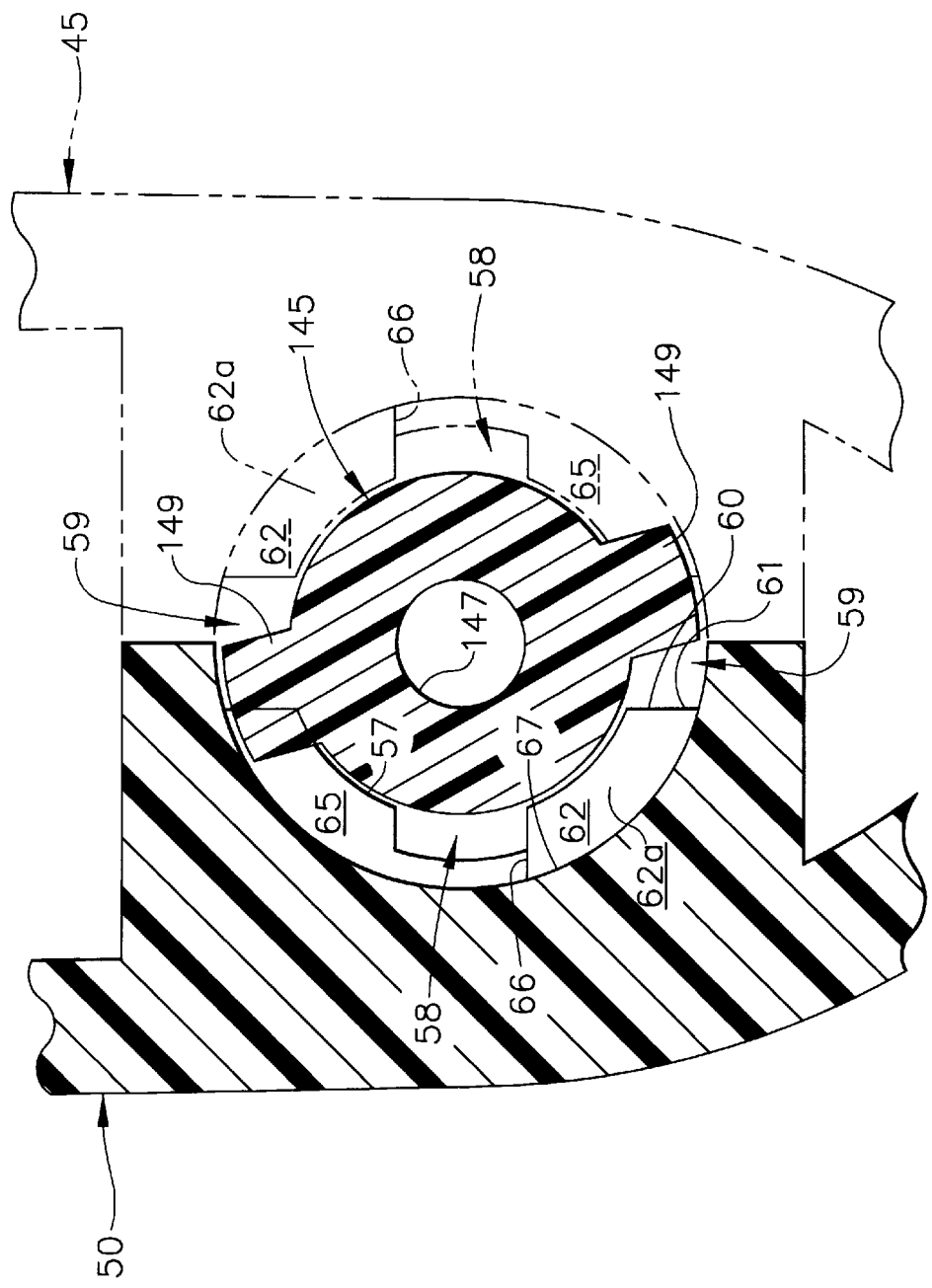
FIG. 16 is a section view of a portion of the assembled handheld surgical instrument of FIG. 1 showing the position of the plunger relative to the crosshatched left handle cover and the phantom lined right handle cover when the releasable locking mechanism is in the process of becoming unlocked.

FIGS. 15 and 16 show the process of switching the releasable locking mechanism 115 from the locked position to the unlocked position with a second reciprocation of the release trigger 120. In FIG. 15, the actuation member 105 is squeezed proximally to a position adjacent to the handle body assembly 40. The movement of the actuation member 105 moves the cam button 135 and the partially engaged plunger 145 proximally into the handle body assembly 40. As the cam button 135 and plunger 145 move proximally, the cam teeth 140 remain partially engaged with the plunger teeth 153 (see FIG. 14) until the elements of the releasable locking mechanism 115 reach the position previously shown in FIG. 12. Additional distal movement of the elements of the releasable locking mechanism 115 enable the distal plunger peaks 151 of the plunger 145 to move proximally past the unlocking edge s 64a of the vertical surfaces 60 (FIG. 4) of the right and left handle covers 45 and 50. This movement rotationally unlocks the plunger 145 and the plunger teeth 153 slide on the cam teeth 140 and rotate plunger 145 to the fully engaged position shown in FIGS. 15 and 16. This otation moves the lower plunger rib 149 into view. The fully engaged plunger 145 and cam button 135 continue to move distally within the handle body assembly 40 to the positions of FIGS. 15 and 16. The locking tab 155 is biased clockwise (see arrow) by the plunger 145 and is unlocked. It is of note that in FIG. 16 the plunger ribs 149 of the plunger 145 are shown rotated to the position described above and that this location is partially over the unlocking ramps 65.

When the actuation member 105 is released by the operator from the fully squeezed position shown in FIGS. 15 and 16, the moveable components of the releasable locking mechanism 115 move distally under the bias of the locking tab spring 165. The distal motion of the releasable locking mechanism 115 brings the plunger peaks 151 of the plunger 145 into sliding contact with the sloped unlocking ramps 65 of the right and left handle covers 45 and 50. This sliding contact rotates the plunger 145 to the unlocked position of FIG. 6 wherein the distal plunger peaks 151 of the plunger ribs 149 are captured within a pair of horizontally opposed valleys formed from the intersection of the stop surfaces 66 and the unlocking ramps 65. The cam button 135 and actuation member 105 return to the extended position of FIG. 6, thus completing the second unlocking reciprocation.

While preferred embodiments of the present invention have been shown and described herein, it will be obvious to those skilled in the art that such embodiments are provided by way of example only. Numerous variations, changes, and substitutions will now become evident to those skilled in the art without departing from the invention. Accordingly, the scope of the invention can only be determined in connection with the appended claims set forth below.

What is claimed is:

1. A surgical instrument for grasping and clamping tissue comprising:

a handle body assembly;

an elongated shaft having a proximal end and a distal end and connected to said handle body assembly at the proximal end of said shaft;

an end effector having at least one moveable member located at the distal end of said shaft;

an actuation member having a proximal end, said actuation member moveable toward and away from said handle body assembly and operatively connected to said end effector for actuating movement of said at least one moveable member;

a locking tab on said handle body assembly and having a hole therethrough, said locking tab being moveable between a locked position and an unlocked position;

a locking rod having a proximal end and a distal end, said locking rod being fixed to said actuation member at the proximal end of said actuation member, wherein at least the distal end of said locking rod is moveably engaged with said locking tab through said hole when said locking tab is in the unlocked position so as to allow movement of said actuation member towards and away from said handle body assembly, and said locking rod is fixed relative to said locking tab when said locking tab is in the locked position so as to prevent movement of said actuation member away from said handle body assembly; and a release trigger having an elongated trigger member and operably coupled to said locking tab, said release trigger moveable in and extending from said handle body assembly from a first position spaced away from said handle body to a second position adjacent to said handle body, said release trigger being biased toward the first position, and said release trigger being reciprocable when initially squeezed toward said handle body assembly from the first position to the second position and subsequently released from the second position back to the first position, wherein consecutive reciprocations of said release trigger alternates said locking tab between said locked position and said unlocked position and said release trigger has a rib extending longitudinally on said trigger member for preventing said release trigger from rotating in said handle body assembly about said trigger member.

2. The surgical instrument of claim 1 wherein said release trigger is operably coupled to said locking tab in an arcuate path within said handle body assembly.

3. The surgical instrument of claim 2 further comprising a trigger spring on said handle body assembly for biasing said release trigger toward the first position.

4. The surgical instrument of claim 3 wherein said release trigger has a distal finger pad.

5. The surgical instrument of claim 4 wherein said elongated trigger member extends proximally from said distal finger pad into said handle body assembly.

6. The surgical instrument of claim 5 further comprising a locking tab spring operably connected to said handle body assembly and said locking tab, said locking tab spring biasing said locking tab towards the locked position and locking said locking tab with said locking rod when said locking tab is in the locked position.

7. The instrument of claim 6 wherein said locking tab has a rectangular hole.

8. The instrument of claim 7 wherein said locking rod has a rectangular cross section, and said rectangular hole of said locking tab receives said locking rod.

9. The instrument of claim 8 wherein said locking rod is curved.

10. The instrument of claim 9 wherein said locking rod is formed from an engineering thermoplastic.

11. The instrument of claim 10 wherein said locking rod is integrally formed with at least one part of said actuation member.

12. The instrument of claim 10 wherein said actuation member has a finger loop.

* * * * *